(12) United States Patent
Hjelt et al.

(10) Patent No.: US 7,278,966 B2
(45) Date of Patent: Oct. 9, 2007

(54) SYSTEM, METHOD AND COMPUTER PROGRAM PRODUCT FOR MANAGING PHYSIOLOGICAL INFORMATION RELATING TO A TERMINAL USER

(75) Inventors: Kari Hjelt, Espoo (FI); Santtu Naukkarinen, Espoo (FI); Jukka Nihtilä, Espoo (FI); Tapani Ryhänen, Helsinki (FI); Timo Vitikainen, Espoo (FI)

(73) Assignee: Nokia Corporation, Espoo (FI)

( * ) Notice: Subject to any disclaimer, the term of this patent is extended or adjusted under 35 U.S.C. 154(b) by 0 days.

(21) Appl. No.: 10/853,702

(22) Filed: May 25, 2004

(65) Prior Publication Data

US 2005/0171410 A1    Aug. 4, 2005

Related U.S. Application Data

(60) Provisional application No. 60/540,607, filed on Jan. 31, 2004.

(51) Int. Cl.
*A61B 5/00* (2006.01)

(52) U.S. Cl. ............... 600/300; 600/301; 128/920; 482/8

(58) Field of Classification Search ........ 600/300–301, 600/401, 595; 128/903–905, 920–921; 705/2–4; 340/573.12; 482/4, 8–9
See application file for complete search history.

(56) References Cited

U.S. PATENT DOCUMENTS

| | | |
|---|---|---|
| 5,447,524 A | 9/1995 | Alt |
| 5,524,637 A | 6/1996 | Erickson |
| 5,749,372 A | 5/1998 | Allen et al. |
| 5,976,083 A | 11/1999 | Richardson et al. |
| 5,989,200 A | 11/1999 | Yoshimura et al. |
| 6,122,960 A | 9/2000 | Hutchings et al. |
| 6,356,856 B1 | 3/2002 | Damen et al. |
| 6,396,416 B1 | 5/2002 | Kuusela et al. |

(Continued)

FOREIGN PATENT DOCUMENTS

EP    1 027 860 A1    8/2000

(Continued)

OTHER PUBLICATIONS

*Nokia 5140 mobile phone adds mobility to Outdoor Adventure, Sport and Fitness*; Feb. 2, 2004; Nokia.com Press Releases; available at <http://press.nokia.com/PR/200402/932564_5/html> (visited Feb. 2, 2004).

Primary Examiner—Max F. Hindenburg
Assistant Examiner—Michael C Astorino
(74) Attorney, Agent, or Firm—Alston & Bird LLP

(57) ABSTRACT

A system for managing physiological information includes a mobile terminal and at least one destination. The terminal is capable of transferring physiological information relating to a terminal user. The destination(s), in turn, are capable of receiving the physiological information and performing at least one operation based upon the physiological information. The destinations can return content to the terminal, where the content is selected based upon the operation(s) performed by the destination(s). Upon receiving the content, then, the terminal is also capable of performing at least one operation based upon the content. The system can also include a mobile station for facilitating the transfer of physiological information and content between the terminal and the destination(s).

70 Claims, 16 Drawing Sheets

U.S. PATENT DOCUMENTS

| | | |
|---|---|---|
| 6,478,736 B1 * | 11/2002 | Mault .................... 600/300 |
| 6,497,638 B1 * | 12/2002 | Shea ........................ 482/8 |
| 6,501,386 B2 | 12/2002 | Lehrman et al. |
| 6,595,929 B2 * | 7/2003 | Stivoric et al. ............ 600/549 |
| 6,635,013 B2 | 10/2003 | Pfeffer |
| 2001/0049470 A1 | 12/2001 | Mault et al. |
| 2002/0019586 A1 | 2/2002 | Teller et al. |
| 2002/0072932 A1 * | 6/2002 | Swamy ........................ 705/2 |
| 2002/0133378 A1 | 9/2002 | Mault et al. |
| 2003/0090389 A1 | 5/2003 | Maeda et al. |
| 2003/0208110 A1 | 11/2003 | Mault et al. |
| 2004/0002634 A1 | 1/2004 | Nihtila |
| 2004/0002662 A1 | 1/2004 | Hjelt et al. |
| 2004/0081110 A1 | 4/2004 | Koskimies |

FOREIGN PATENT DOCUMENTS

| | | |
|---|---|---|
| EP | 1 138 259 A2 | 10/2001 |
| EP | 1 193 494 A1 | 4/2002 |
| EP | 1 374 766 A1 | 1/2004 |
| WO | WO 02/00111 A1 | 1/2002 |
| WO | WO 03/055389 A1 | 7/2003 |

* cited by examiner

SYSTEM, METHOD AND COMPUTER PROGRAM PRODUCT FOR MANAGING PHYSIOLOGICAL INFORMATION RELATING TO A TERMINAL USER

CROSS-REFERENCE TO RELATED APPLICATIONS

The present application claims priority from U.S. Provisional Patent Application Ser. No. 60/540,607, entitled: SYSTEM AND ASSOCIATED TERMINAL, METHOD AND COMPUTER PROGRAM PRODUCT FOR MONITORING AT LEAST ONE ACTIVITY OF A USER, filed on Jan. 31, 2004, the contents of which are incorporated herein by reference in its entirety.

FIELD OF THE INVENTION

The present invention generally relates to systems and methods for monitoring activities of a user and, more particularly, relates to systems, associated methods and computer program products for managing physiological information relating to activities of a user.

BACKGROUND OF THE INVENTION

People follow exercise programs for a variety of reasons. These reasons include maintaining general well-being, assisting a weight loss program and preparation for a particular sporting event, such as a marathon. Such programs need to be carefully formulated and managed if the desired effect is to be achieved, and the exerciser is to avoid injury. It is known, for example from U.S. Pat. No. 6,635,013, to use a computer to provide a user with an exercise program. However, this system merely provides printed static instructions. Consequently, a person who requires more interactive exercise program development must employ a personal fitness trainer, which can be inconvenient and costly.

Systems and apparatuses have been developed to provide a fitness program that is cost-effective and convenient. One such apparatus is disclosed by Great Britain (GB) Patent Application No. 0326387.8, entitled: *Apparatus and Method for Providing a User with a Personal Exercise Program*, filed Nov. 12, 2003, the contents of which are hereby incorporated by reference in its entirety. As disclosed by GB 0326387.8, an exercise assistance apparatus includes a user interface, which can comprise a wireless communication receiver, and a processor, which can comprise a mobile phone. The apparatus is configured for generating an exercise program based upon physical parameters, such as physiological information (e.g., information relating to aerobic fitness) of a user, where the exercise program can include aerobic fitness and/or strength enhancing exercises. The apparatus can also be configured for controlling the user interface to provide guidance to the user during performance of a generated program.

The apparatus can be configured to generate a program that includes a plurality of exercise definitions, each including a variable exercise duration parameter. The apparatus can set the variable parameter based upon the physiological information, such as the input information relating to aerobic fitness. The apparatus can also be configured to compute an exercise duration by multiplying a base duration by an aerobic fitness value for the user. The aerobic fitness value, in turn, can be determined based upon the input physiological information, and thereafter modified, such as at predetermined times (e.g., intervals of three to eight weeks), based upon physiological information that can be input at the end of an exercise of the generated program. More particularly, for example, the aerobic fitness value can be modified by determining an expected performance, determining actual performance from the physiological information received after exercises, comparing the expected and actual performances, and thereafter increasing or decreasing the aerobic fitness value based upon the comparison.

The apparatus can also be configured to generate a program by selecting a mix of exercises of different intensity classes, where the ratios of the mix of intensities are determined by the aerobic fitness value. If so desired, the ratios can be further determined based upon the number of exercise sessions per week in the generated program. The apparatus can be configured to select a varied selection of exercises in an intensity class from a predetermined list of exercises, such as by selecting exercises for a terminal period of the program that represent a reduction in intensity.

The apparatus can further be configured to generate a program by selecting exercises based upon a strength value, where the strength value can be determined based upon the input physiological information. In such instances, the apparatus can be configured to select exercises for the program that become successively harder during the program. And as indicated above, the apparatus can be configured to determine a varied selection of exercises from a predetermined list of exercises.

Whereas an apparatus such as that disclosed by GB 0326387.8 adequately provides a fitness program that is cost-effective and convenient. It is always desirable to improve upon such apparatuses. Thus, it would be desirable to design an activity monitor capable of deriving physiological information relating to a user performing an exercise, where the activity monitor includes a means for wirelessly communicating the derived physiological information, such as to an exercise assistance apparatus like that disclosed by GB 0326387.8. In this regard, it would be further desirable to provide a system and method of managing the derived physiological information.

SUMMARY OF THE INVENTION

In light of the foregoing background, embodiments of the present invention provide a terminal and associated method and computer program product for monitoring at least one activity of a user. Although the user typically comprises a person, in accordance with embodiments of the present invention, the user can alternatively comprise any of a number of entities capable of performing one or more activities. For example, the user can comprise a dog, cat, horse, rabbit, goat or other animal capable of performing one or more activities, many activities being performed much like a person.

Embodiments of the present invention are capable of monitoring the fitness activities of a user, and enabling the user to manage his or her personal fitness goals. More particularly, the terminal is capable of deriving physiological information relating to the terminal user. Thereafter, embodiments of the present invention are capable of managing the physiological information so as to provide for an enhanced user experience by permitting the terminal to transfer one or more pieces of physiological information to one or more destinations. For example, embodiments of the present invention permit terminal users to share physiological information with one another by transferring physiological information among a number of respective terminals. Additionally, or alternatively, embodiments of the present invention permit the terminal user to transfer physiological information to one or more destinations such that the destination(s) can provide content to the terminal based upon the physiological information, such as an adjusted exercise program and/or alerts to perform activities of an exercise program.

According to one aspect of the present invention, a system is provided for managing physiological information. The system includes a mobile terminal and at least one destination. The terminal is capable of transferring physiological information relating to a terminal user. In this regard, the terminal can also be capable of deriving the physiological information. The destination(s), in turn, are capable of receiving the physiological information and performing at least one operation based upon the physiological information. The destinations can return content to the terminal, where the content is selected based upon the operation(s) performed by the destination(s). Upon receiving the content, then, the terminal is also capable of performing at least one operation based upon the content. In one typical context, the destination(s) include at least one other mobile terminal. In such instances, the other mobile terminal(s) can be capable of returning physiological information relating to other user(s) of the other terminal(s).

More particularly, for example, the destination(s) can be capable of performing operation(s) including adjusting an exercise program and/or setting at least one alert based upon an exercise schedule. In such instances, the destination(s) can further be capable of returning the adjusted exercise program and/or alerts to the terminal. In turn, the terminal can then be capable of performing operation(s) including modifying a calendar of the user, the calendar being capable of reflecting workout schedule(s) of the adjusted exercise program. Additionally or alternatively, the terminal can be capable of notifying the user of the adjusted exercise program, and/or executing the alert(s). To enhance the user's experience during performance of the activit(ies), the terminal can be capable of transferring physiological information, with the destination(s) being capable of adjusting the exercise program and returning the adjusted exercise program to the terminal, and the terminal notifying the user of the adjusted exercise program, all during performance of the activit(ies) by the user.

The system can also include a mobile station for facilitating the transfer of physiological information and content between the terminal and the destination(s). More particularly, the mobile station can be capable of receiving the physiological information from the terminal, and thereafter transmitting the physiological information to the destination (s). In turn, the mobile station can also be capable of receiving content from the destination(s), and thereafter returning the content to the terminal.

Before the terminal transfers physiological information, the terminal or mobile station can be capable of initiating the transfer of physiological information based upon presence information related to the user. More particularly, the terminal or mobile station can be capable of monitoring presence information related to the user, and initiating the transfer when the presence information is indicative of the user performing the at least one activity. For example, the terminal or mobile station can be capable of initiating the transfer when performance of the activit(ies) is detected. In this regard, the terminal or mobile station can be capable of initiating the transfer when the presence information indicates that the mobile terminal is deriving physiological information relating to the user. Alternatively, for example, the terminal or mobile station can be capable of initiating the transfer when a current time matches a predefined time set for the user to perform the at least one activity. In yet another alternative example, the terminal or mobile station can be capable of initiating the transfer when a location of the terminal matches a location where the user is capable of performing the activit(ies).

According to other aspects of the present invention, a mobile terminal, mobile station, method and computer program product are provided for managing physiological information. Therefore, embodiments of the present invention provide a system, mobile terminal, mobile station, method and computer program product for managing physiological information relating to a terminal user. As indicated above and explained below, embodiments of the present invention are capable of managing the physiological information by permitting the terminal to transfer physiological information to destinations, which are capable of performing operations based upon the physiological information and returning content to the terminal. Therefore, the system, mobile terminal, mobile station, method and computer program product of embodiments of the present invention solve the problems identified by prior techniques and provide additional advantages.

BRIEF DESCRIPTION OF THE DRAWINGS

Figure 1:
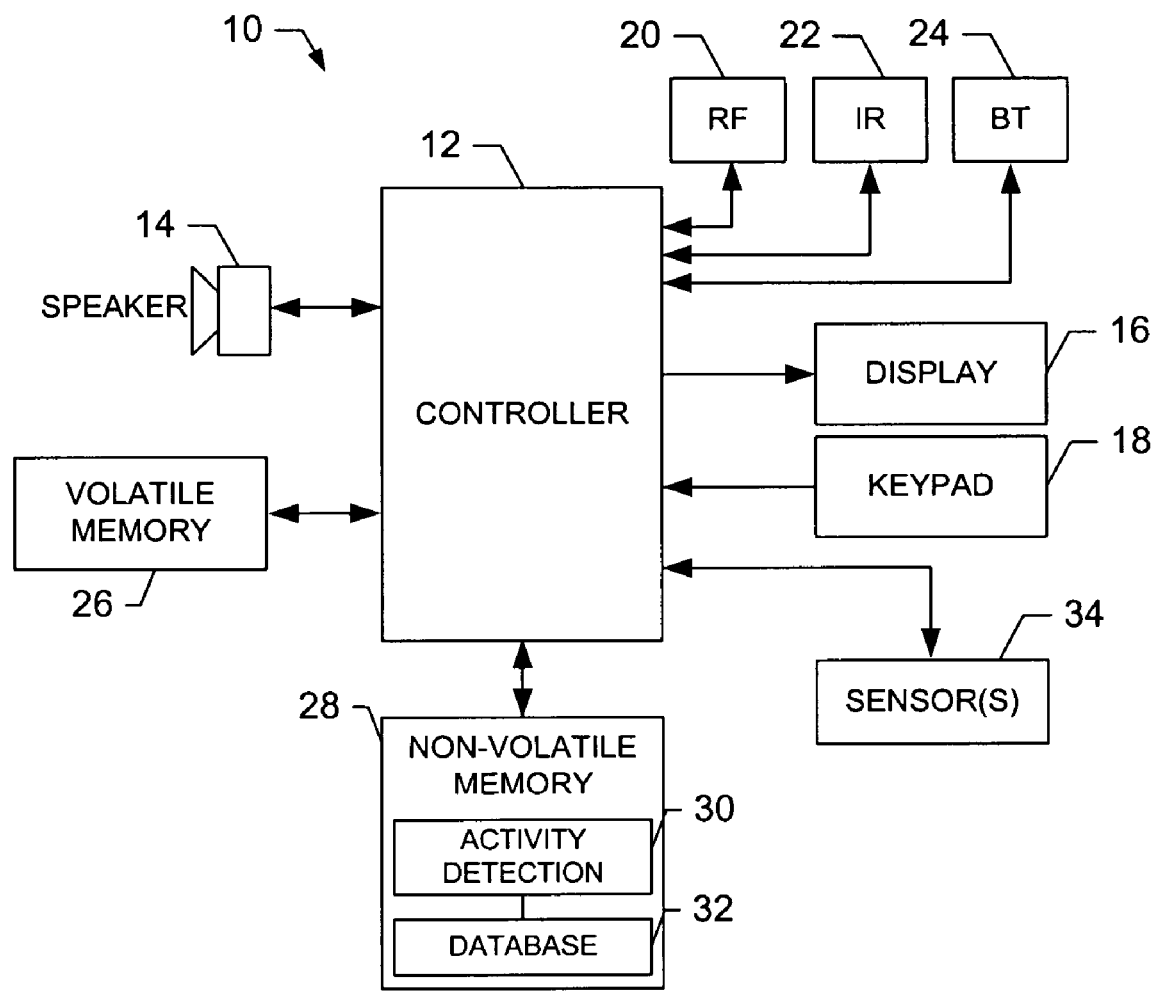
Figure 3:
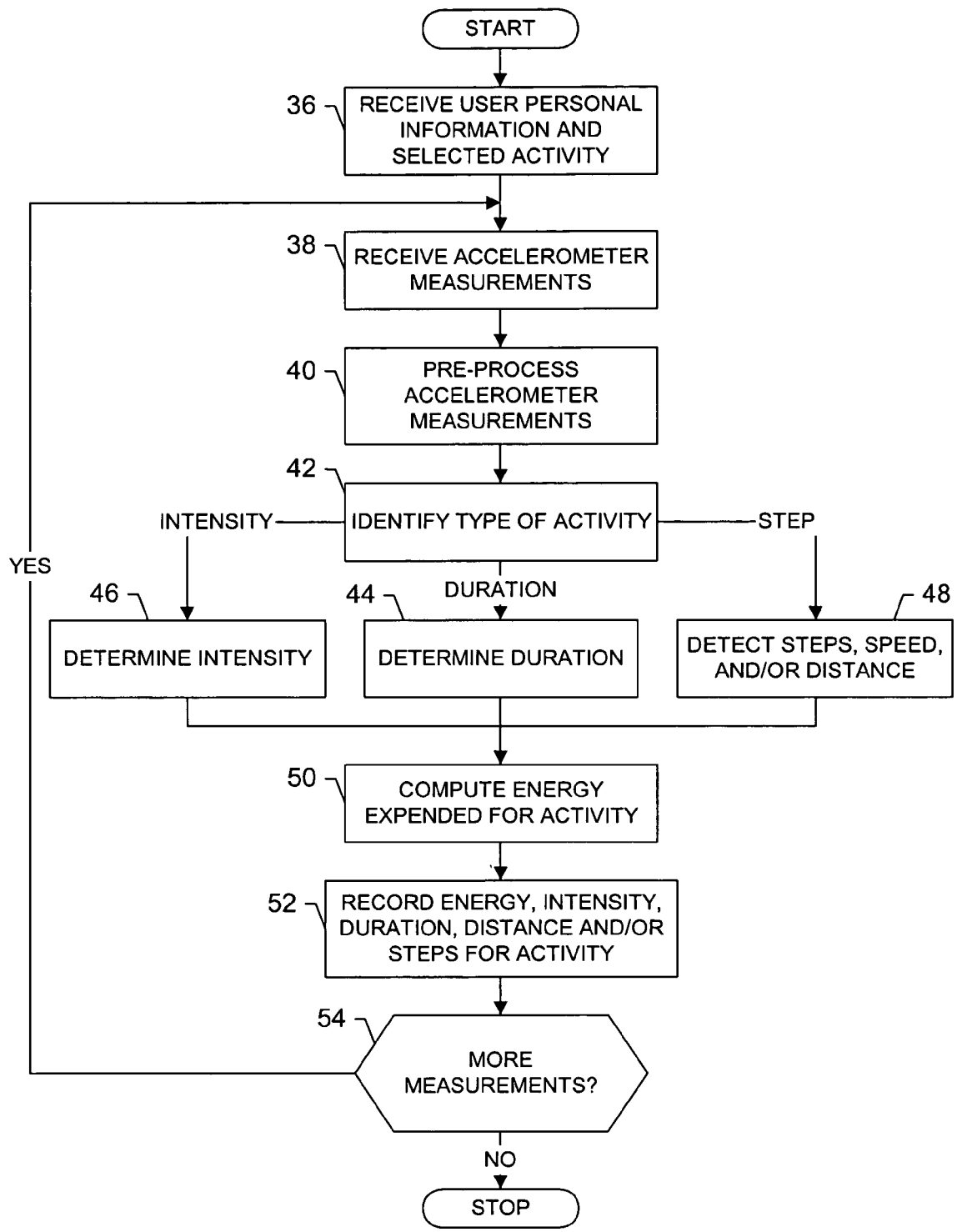
Figure 4A:
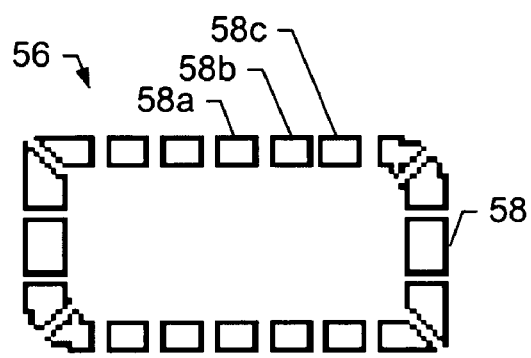
Figure 4B:
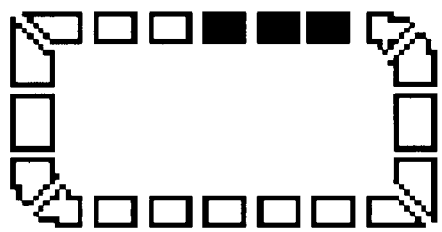
Figure 4C:
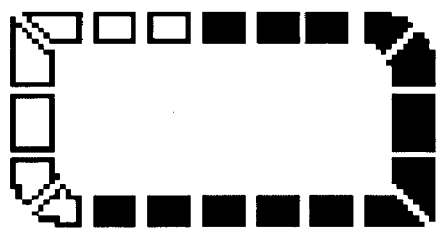
Figure 4D:
Figure 5:
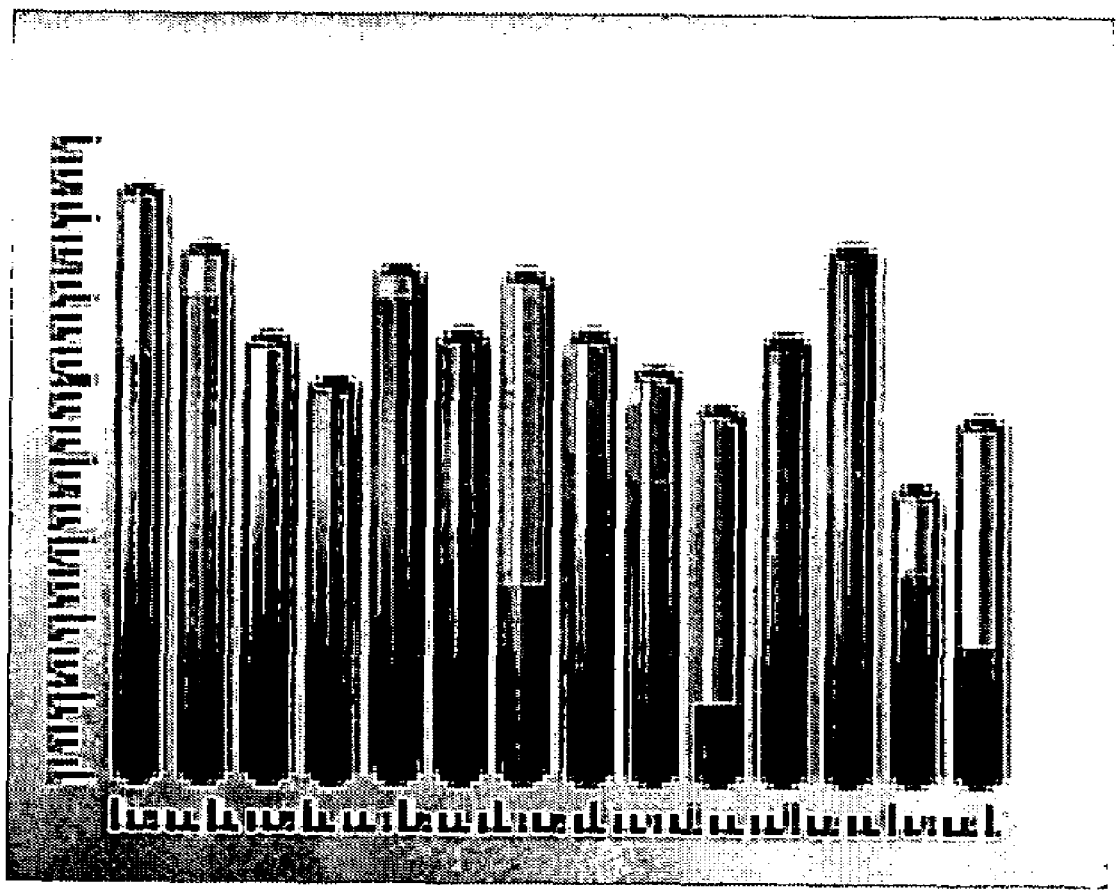
Figure 15:
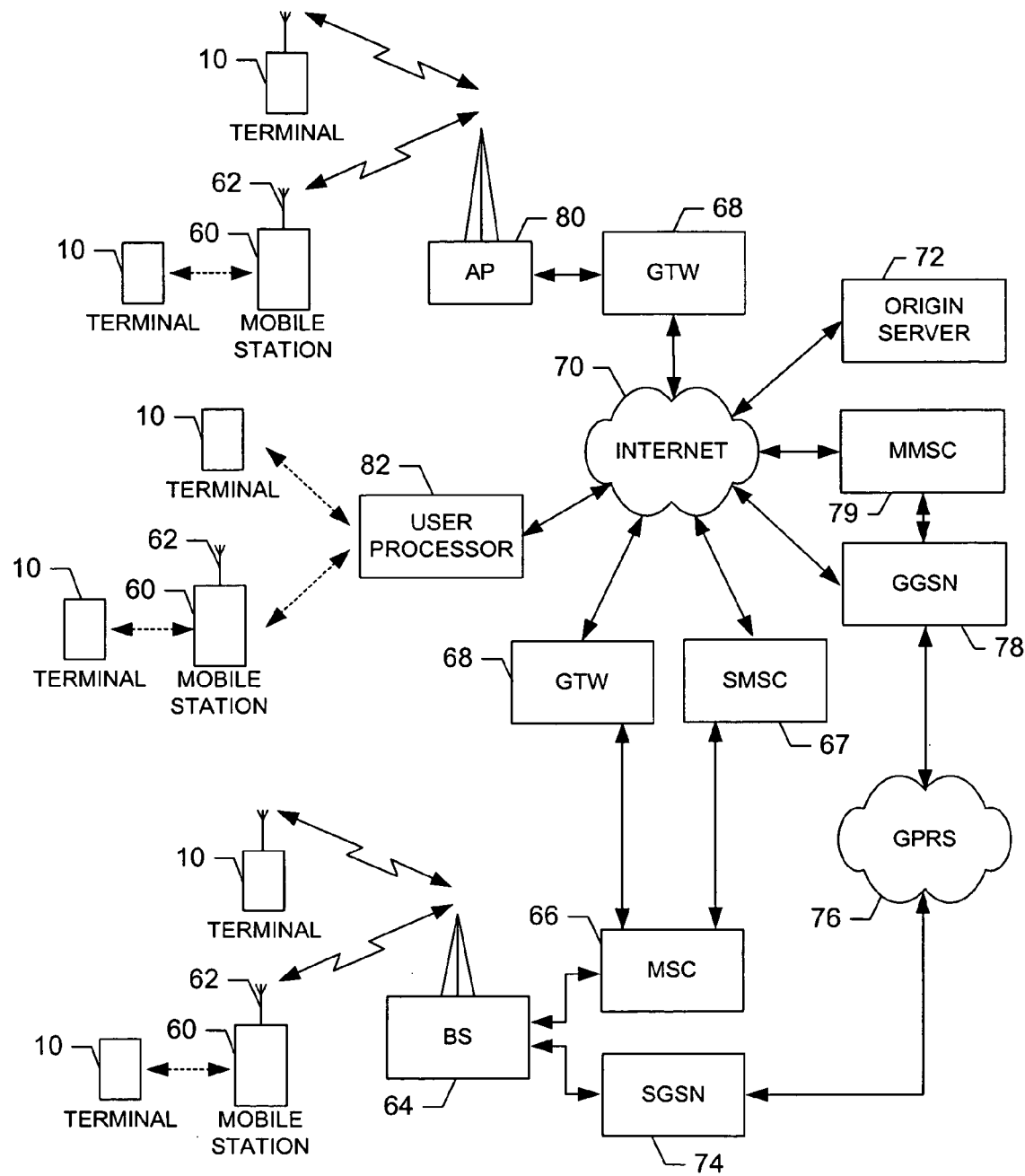
Figure 16:
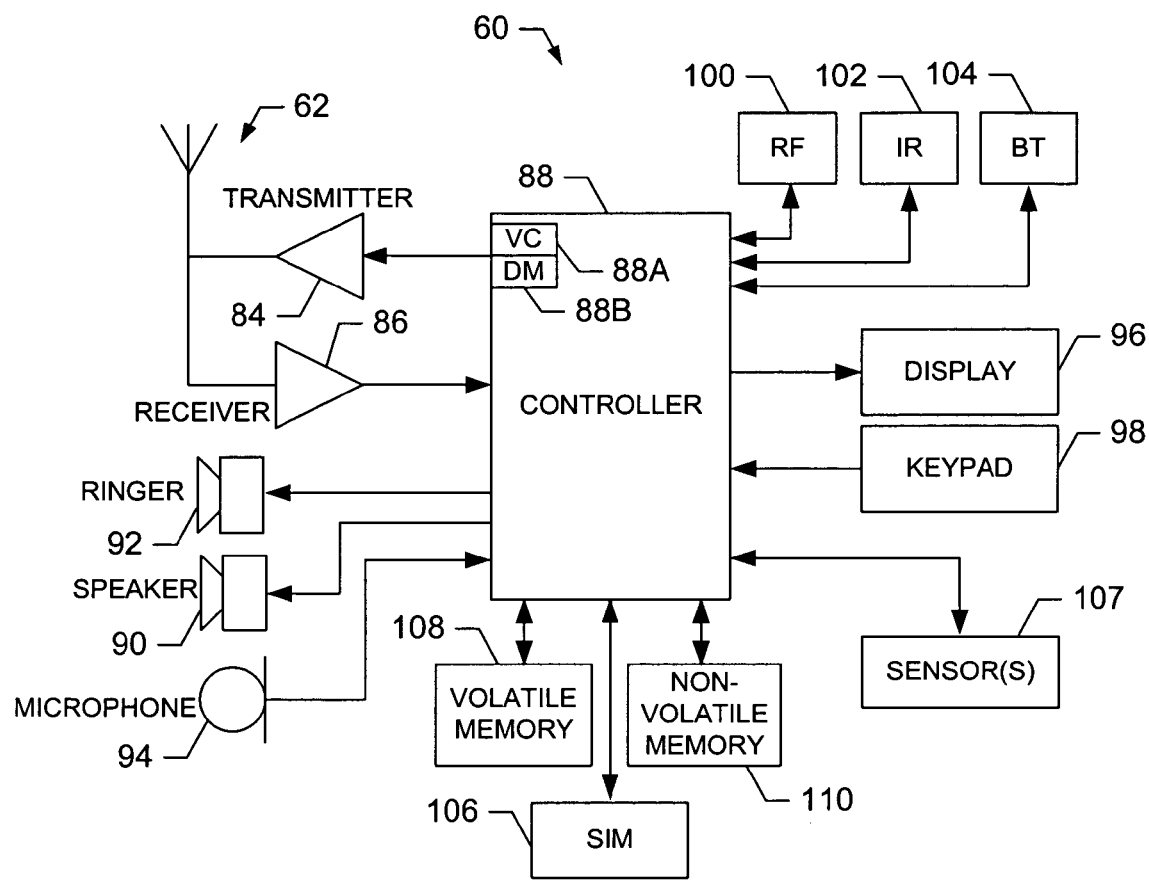
Figure 17:
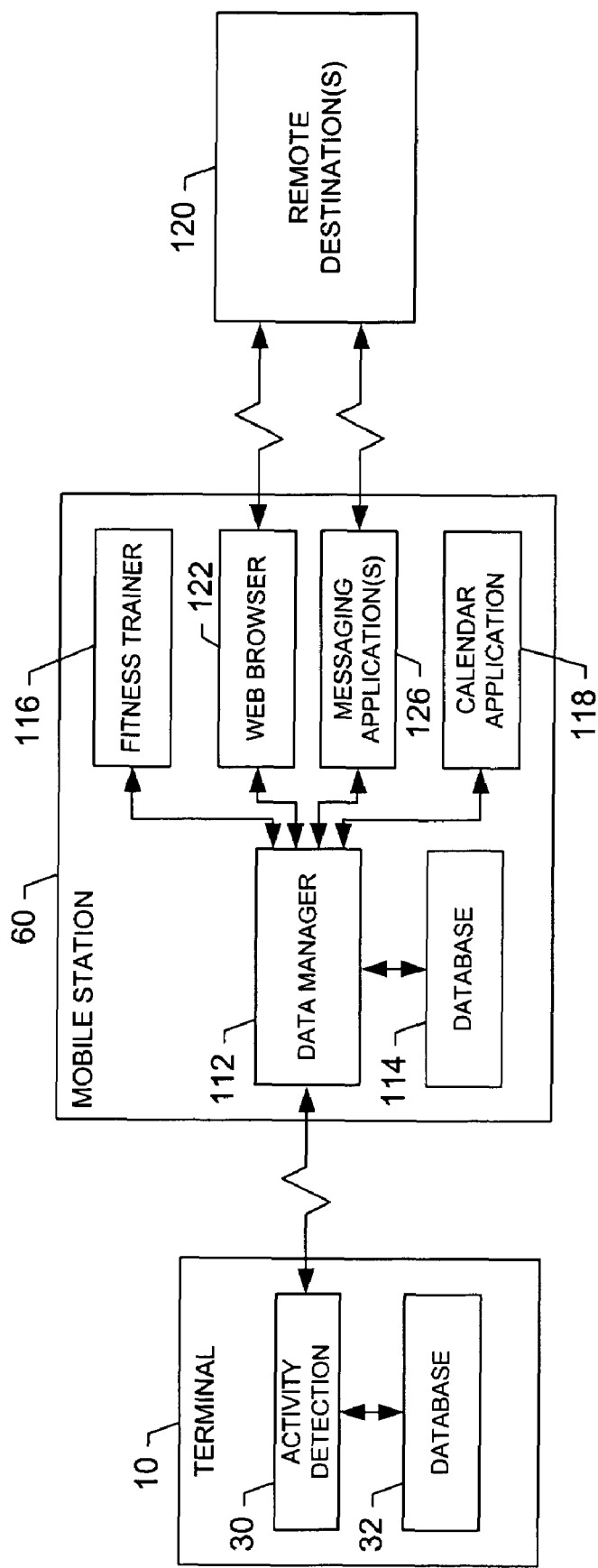
Figure 18:
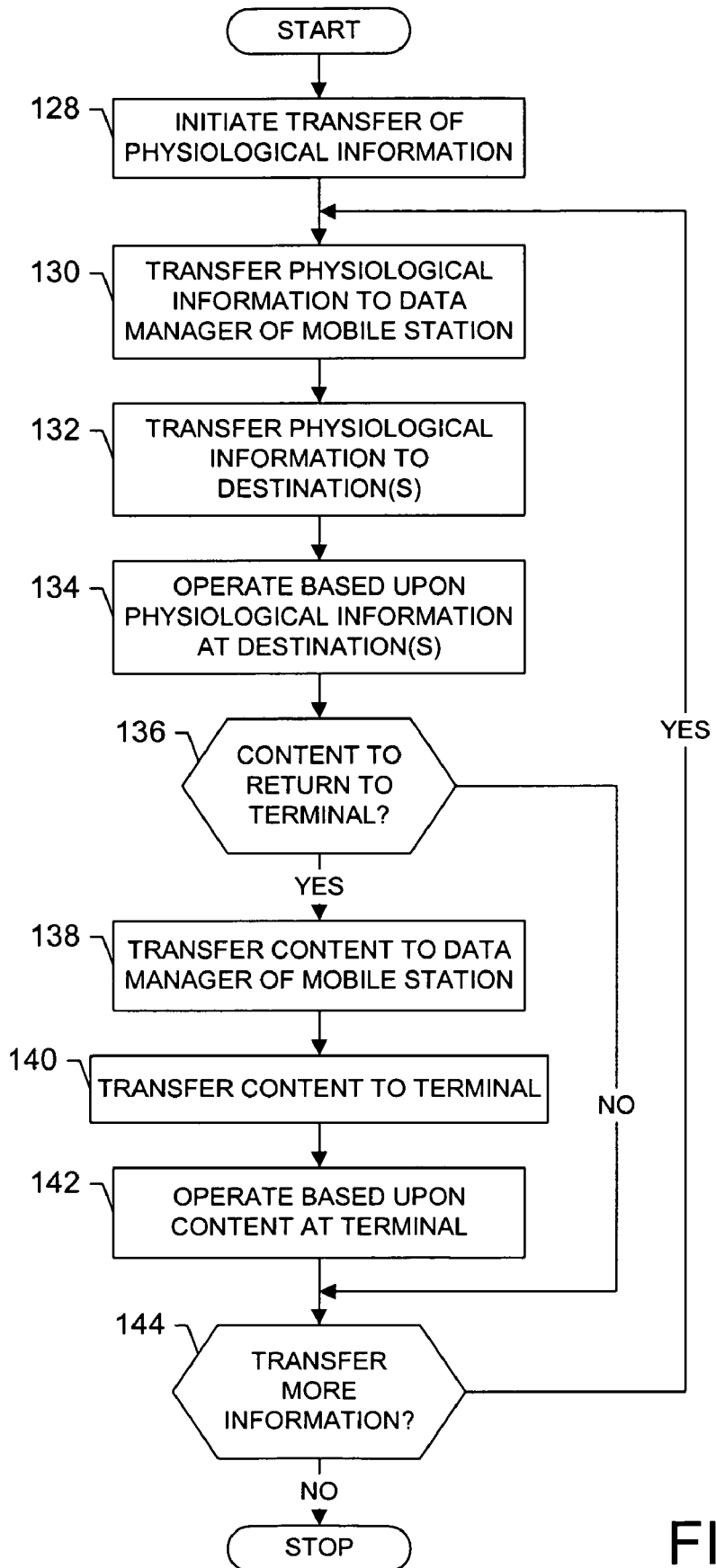

Having thus described the invention in general terms, reference will now be made to the accompanying drawings, which are not necessarily drawn to scale, and wherein:

FIG. 1 is a schematic block diagram of a terminal of one embodiment of the present invention;

FIGS. 2A-2E are schematic illustrations of a terminal placed in proximity to a user, in accordance with various embodiments of the present invention;

FIG. 3 is a flowchart illustrating various steps in a method of monitoring at least one activity of a user, in accordance with one embodiment of the present invention;

FIGS. 4A-4D are schematic illustrations of a graphical representation of a goal of the user where each of a number of sections of the graphical representation represents a successive percentage of the goal and can be altered to reflect the user achieving the respective percentage;

FIG. 5 is a schematic bar graph illustrating pieces of physiological information collected by the terminal over a number of successive time periods;

FIGS. 6A-6C, 7, 8A-8D, 9A-9D, 10, 11, 12A-12D, 13 and 14 are schematic illustrations of the terminal of embodiments of the present invention and various exemplar displays presented during operation of the terminal;

FIG. 15 is a schematic block diagram of a wireless communications system according to one embodiment of the present invention including a mobile network and a data network to which a terminal is bi-directionally coupled through wireless RF links;

FIG. 16 is a schematic block diagram of a mobile station, in accordance with one embodiment of the present invention;

FIG. 17 is a functional block diagram of a terminal providing or otherwise transferring one or more pieces of physiological information to one or more destinations via a mobile station, in accordance with one embodiment of the present invention; and FIG. 18 is a flowchart including various steps in a method of managing physiological information computed or otherwise derived by a mobile terminal, in accordance with one embodiment of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

FIG. 1 illustrates a schematic block diagram of a terminal 10 in accordance with one embodiment of the present invention. It should be understood, that the terminal illustrated and hereinafter described is merely illustrative of one type of terminal that would benefit from the present invention and, therefore, should not be taken to limit the scope of the present invention. While several embodiments of the terminal are illustrated and will be hereinafter described for purposes of example, other types of terminals, such as mobile telephones, portable digital assistants (PDAs), pagers, and other types of voice and text communications systems, can readily employ the present invention.

As shown, the terminal 10 includes a processor such as a controller 12. The controller includes the circuitry required for implementing the functions of the terminal in accordance with embodiments of the present invention, as explained in greater detail below. For example, the controller may be comprised of a digital signal processor device, a microprocessor device, and/or various analog to digital converters, digital to analog converters, and other support circuits. The control and signal processing functions of the terminal are allocated between these devices according to their respective capabilities. The controller may also include the functionally to operate one or more software applications. In addition to the controller, the terminal also includes a user interface that may include, for example, a conventional earphone or speaker 14 capable of being driven by the controller to present various audible tones during operation of the terminal. The user interface may also include a display 16 and a user input interface, both of which are also coupled to the controller. Although not shown, the user interface can further include a microphone capable of receiving, for example, voice input. The user input interface, which allows the terminal to receive data, can comprise any of a number of devices allowing the terminal to receive data, such as a keypad 18, a touch display (not shown) or other input device. In embodiments including a keypad, the keypad can include one or more keys used for operating the terminal.

The terminal can also include one or more means for sharing and/or obtaining data from electronic devices in accordance with any of a number of different wireline and/or wireless techniques, as also explained below. For example, the terminal can include a radio frequency (RF) transceiver 20 and/or an infrared (IR) transceiver 22 such that the terminal can share and/or obtain data in accordance with radio frequency and/or infrared techniques. Also, for example, the terminal can include a Bluetooth (BT) transceiver 24 such that the terminal can share and/or obtain data in accordance with Bluetooth transfer techniques. Although not shown, the terminal may additionally or alternatively be capable of transmitting and/or receiving data from electronic devices according to a number of different wireline and/or wireless networking techniques, including LAN and/or WLAN techniques.

The terminal 10 can further include memory, such as a volatile memory 26 and/or non-volatile memory 28. The non-volatile memory, for example, can comprise embedded or removable multimedia memory cards (MMC's), Memory Sticks manufactured by Sony Corporation, EEPROM, flash memory, hard disk or the like. The memories can store any of a number of pieces of information, and data, used by the terminal to implement the functions of the terminal. For example, the memories can store activity detection application 30 capable of operating on the terminal to monitor the fitness activities of a user of the terminal, and manage the user's personal fitness goals. In this regard, the memories can also store a database 32 including, for example, personal information regarding a user of the terminal, such as date of birth, gender, height and/or weight, as well as a step length for the user when walking and/or running. In addition, for example, the database can include personal fitness goals of the user, such as a one-time and/or weekly goal for an amount of time performing one or more activities, a number of steps taken in performing the activit(ies), a number of calories burned in performing the activit(ies), and/or a distance traveled in performing the activit(ies). Likewise, for example, the database can include an amount of time spent by the user in performing one or more activities for a given time period, a number of steps taken in performing the activit(ies), a number of calories burned in performing the activit(ies), and/or a distance traveled in performing the activit(ies).

The terminal may also have one or more sensors 34 for sensing the ambient conditions of the terminal or terminal user, or one or more physiological conditions of the terminal user. In this regard, the terminal may include sensors such as, for example, a heart rate sensor, a positioning sensor, a touch sensor, an audio sensor, a compass sensor, an ambient light sensor, an ambient pressure senor, and/or an ambient temperature sensor. The positioning sensor can comprise, for example, a global positioning system (GPS) sensor. Additionally, or alternatively, the positioning sensor can comprise, for example, a radio beacon triangulation sensor that determines the location of the wireless device by means of a network of radio beacons, base stations, or access points, as is described for example, in Nokia European patent EP 0 767 594 A3, entitled: *Terminal Positioning System*, published on May 12, 1999, the contents of which are hereby incorporated by reference in its entirety.

As will be appreciated, the sensors 34 can also be located in accessory-like terminal 10 covers and/or in a wireless accessory such as a Bluetooth-enabled device. The sensors may further be located in the environment such as in the user's rooms or vehicles, with data collected by such sensors being transferred to the terminal. Also, information capable of being measured by the terminal, such as the time duration of use of the terminal, can be received as sensor data by the terminal. For more information on such sensors, see U.S. patent application Ser. No. 09/854,628, entitled: *Context Sensitive Web Services*, filed May 15, 2001, which published on Nov. 21, 2002 as U.S. Patent Application Publication No. 2002/0173295, the contents of which are hereby incorporated by reference in its entirety. Although the terminal can include any of a number of different sensors, in one typical embodiment, at least one of the sensors comprises a two or three-axis acceleration sensor (accelerometer).

Figure 2A:
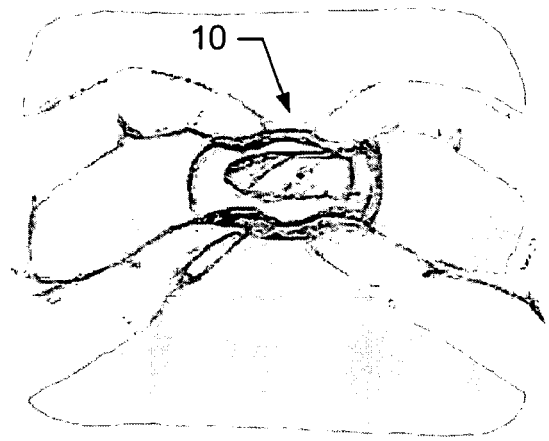
Figure 2B:
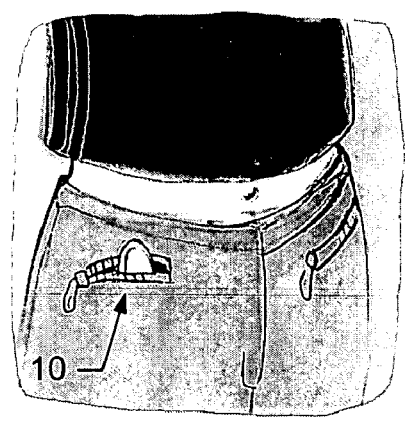
Figure 2C:
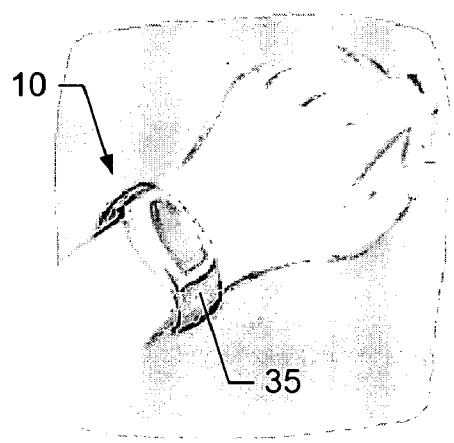
Figure 2D:
Figure 2E:
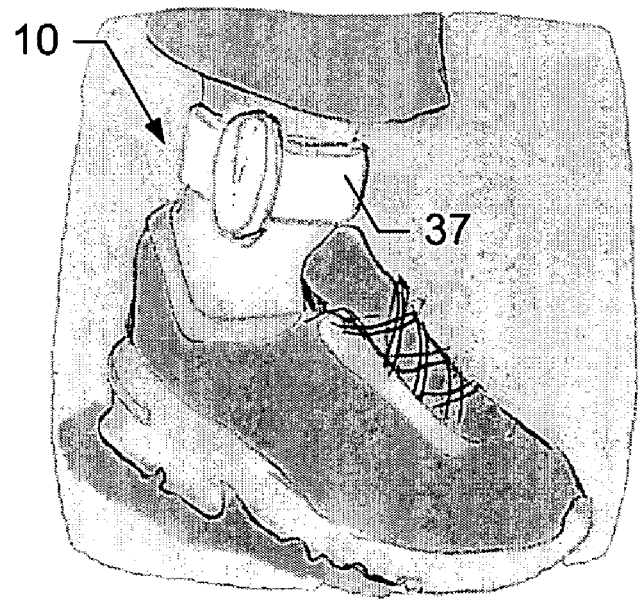

As indicated above, and shown in FIG. 2A, the terminal 10 of embodiments of the present invention is capable of being embodied in a portable package. The terminal can therefore be placed in relatively close proximity to the user. As shown in FIG. 2B, for example, the terminal can be carried in a pocket of clothing of the user. Alternatively, the terminal can be belted or otherwise strapped to a wrist, waist or ankle of the user, as shown in FIGS. 2C, 2D and 2E, respectively. In yet a number of other alternatives, for example, the terminal can be belted or otherwise strapped to an arm or leg of the user, hung from the user's neck, or clipped to clothing of the user. As will be appreciated, in many instances of placing the terminal in close proximity to the user, the terminal additionally includes a strap, belt, clip, lanyard or the like. For example, as shown in FIGS. 2C and 2E, when the terminal is strapped to the wrist or ankle of the user, the terminal can be embodied in a portable package that includes a wrist strap 35 or an ankle strap 37, both of which can comprise the same strap. Also, for example, as shown in FIG. 2D, when the terminal is belted around the waist of the user, the terminal can be embodied in a portable package that includes a belt 39.

Operation of the activity detection application 30 will now be described in accordance with embodiments of the present invention. In this regard, as indicated above, the activity detection application can be embodied in software stored in non-volatile memory 28 and operated by the controller 12 of the terminal 10. It should be understood, however, that whereas the activity detection application is typically embodied in software, the activity detection application can alternatively be embodied in firmware, hardware or the like. Generally, and as explained in greater detail below, the activity detection application is capable of interfacing with the sensor(s) 34 of the terminal to receive measurement(s) of the ambient and/or physiological condition(s) of the user, such as to receive heart rate measurements, and/or acceleration measurements indicative of movement over a distance for one or more periods of time. In this regard, the movement may be representative of the user taking one or more steps while performing one or more activities over those period(s) of time. As the activity detection application receives such measurement(s), the activity detection application can be capable of tracking the duration of an activity, the heart rate of the user in performing the activity, the distance moved by the user in performing the activity, the number of steps taken by the user of the distance, and/or the speed of movement of the user. The activity detection application can additionally be capable of computing energy (e.g., calories) expended by the user in performing the activity.

As will be appreciated, measurements received from the sensor(s) 34 may be indicative of the user running or walking while performing one or more of a number of different activities. For example, measurements may be indicative of the user performing activities such as walking, running, dancing, gardening (outdoor housework), performing housework (indoor housework), and/or participating in a sporting activity (e.g., aerobics, badminton, basketball, football, soccer, golf, weight training, hiking, jumping rope, squash, table tennis, tennis, Nordic training, squash, racquet ball, etc.). And as will also be appreciated, a user may expend more or less energy over a given duration, distance and number of steps depending upon the particular activity performed by the user. Thus, as the activity detection application receives measurement(s) of the ambient conditions of the user for each period of time, the activity detection application 30 can be capable of computing the energy expended by the user based upon the activity performed by the user and an intensity level with which the user performed the activity.

More particularly, reference is now to FIG. 3, which illustrates a method of monitoring at least one activity of a user, in accordance with one embodiment of the present invention. In operation, the activity detection application can be executed or otherwise initialized by the terminal 10, such as in response to user input via the user interface (e.g., keypad 18). Thereafter, as shown in FIG. 3, the activity detection application 30 can request, and thereafter receive, personal information from the user, as shown in block 36. The personal information can comprise any of a number of different pieces of information such as, for example, date of birth, gender, height and/or weight, as well as a step length for the user when walking and/or running. In addition to the personal information, the activity detection application can also request, and thereafter receive, selection of an activity the user is or will be performing during operation of the activity detection application. In this regard, the activity detection application may be capable of receiving a selection of any activity. In one typical embodiment, however, the activity detection application presents a list of activities, such as on the display 16 of the terminal, and thereafter receives a selection of one of the activities from the list. For example, the activity detection application can present a list of activities including walking, running, dancing, gardening (outdoor housework), performing housework (indoor housework), or participating in aerobics, badminton, basketball, football, soccer, golf, weight training, hiking, jumping rope, squash, table tennis, tennis, Nordic training, squash or racquet ball. And as explained below, the activity detection application can further present, and receive an "automatic detection" selection that, upon being selected, causes the activity detection application to detect an activity as the user performs the activity without further input from the user.

Irrespective of how the activity detection application 30 receives the user's personal information and selection of activity, the activity detection application can thereafter be operated to monitor the user in performing the selected activity. More particularly, the activity detection application can receive measurements from one or more sensors 34 of the terminal 10, where the sensor(s) are capable of measuring ambient and/or physiological conditions of the user of the terminal. In one typical embodiment shown in block 38 and described hereinbelow for purposes of illustration, the activity detection application receives acceleration measurements, such as down-acceleration (x-axis) and back-acceleration (y-axis) measurements, from an accelerometer. The activity detection application 30 can receive one or more measurements from the sensor(s) 34 at one or more different times during operation. In one embodiment, for example, the activity detection application receives measurements with a 25 Hz sampling frequency. If necessary, each sampled measurement can also be converted from an analog measurement into a digital measurement for subsequent processing by the activity detection application. For example, each sampled measurement can be passed through an analog-to-digital converter that converts the analog sample into a digital sample, such as a 12-bit digital sample representing measurement amplitudes from 0 to 4095.

Although the activity detection application 30 can receive measurements with a given sampling frequency, the activity detection application can be capable of dynamically adjusting the sampling frequency to thereby control power consumption of the terminal 10. For example, the activity detection application can receive measurements from the accelerometer, and if the measurements are below a given threshold, decrease the sampling frequency to thereby reduce power consumption of the terminal. The activity detection application can thereafter increase the sampling frequency if the measurements increase to above the threshold.

As the activity detection application 30 receives measurements from the accelerometer, the activity detection application can preprocess the accelerometer measurements for subsequent use by the activity detection application, as shown in block 40. For example, the activity detection application can limit the measurements to within a given range of measurements, and/or normalize the measurements. More particularly, for example, when the measurements are sampled and converted into 12-bit samples representing amplitudes from 0 to 4095, the activity detection application can limit each measurement, i, to within a range from 1700 to 2500 as follows:

$$\hat{x}_i, \hat{y}_i = \begin{cases} 1700, & x_i, y_i < 1700 \\ x_i, y_i & 1700 < x_i, y_i < 2500, \\ 2500, & x_i, y_i > 2500 \end{cases}$$

where $x_i$ and $y_i$ refer to the ith down-acceleration (x-axis) and back-acceleration (y-axis) measurements from the accelerometer, respectively; and $\hat{x}_i$; and $\hat{y}_i$, refer to the ith range-limited down-acceleration (x-axis) and back-acceleration (y-axis) measurements, respectively. Generally, as used herein unless otherwise stated, $x_i$ and $y_i$ refer to measurements input into a processing step, and $\hat{x}_i$ and $\hat{y}_i$ refer to measurements output from the respective processing step.

Also, as indicated above, the activity detection application 30 can normalize the measurements. For example, the activity detection application can normalize the measurements about a base of zero by reducing each measurement by the average of all of the measurements. Written notationally, then, each measurement can be normalized as follows:

$$\hat{x}_i, \hat{y}_i = x_i, y_i - \frac{1}{N_1} \sum_{k=i-N_1}^{i} x_k, y_k,$$

where $N_1$ equals a number of samples in a sample window block (e.g., 128 samples) (where the mean computation in determining $\hat{x}_i$ and $\hat{y}_i$ can be performed once per sample window block); $x_i$ and $y_i$ refer to the ith measurements for the respective sample window block; and $\hat{x}_i$ and $\hat{y}_i$ normalized measurements for the respective sample window block.

Before or after pre-processing the measurements from the accelerometer, the activity detection application can identify a type of the selected activity, as shown in block 42. In this regard, as will be appreciated, different activities can include different dominating attributes defining the basis for computing the energy expended by the user in performing the respective activities. For example, the energy expended in performing activities such as gardening, weight training, housework and jumping rope can typically be determined based upon the duration over which the user performs the respective activities. For other activities such as dancing, aerobics, badminton, basketball, football, soccer, golf, hiking, squash, table tennis, tennis, Nordic training, squash and racquet ball, the energy expended by the user can typically be determined based upon an intensity with which the user performs the respective activities. Still yet, for activities such as walking and running, the energy expended by the user can be determined based upon the speed of the user in performing the respective activities.

The activity selected by the user (see block 36) can therefore have an associated type based upon the technique for computing the energy expended by the user in performing the selected activity. Although each activity can have any of a number of different types, in one typical embodiment, each activity can be identified as either a duration activity, an intensity activity or a step activity. In contrast to the intensity and step activities, as indicated above, energy expended by the user in performing duration activities can be determined based upon the duration over which the user performs the respective activities. Thus, in general, and more particularly for the duration activities, the activity detection application 30 can be capable of tracking the duration over which the user performs the selected activity, as shown in block 44.

For each intensity activity, on the other hand, an intensity value can be determined for the user in performing the activity, as shown in block 46. The intensity value can be determined in any of a number of different manners. In one embodiment, for example, the intensity value can be determined based upon an average acceleration measurement. More particularly, the intensity value, I, can be determined as follows:

$$I = \frac{1}{N_2} \sum_{k=i-N_2}^{i} |x_k| + |y_k|,$$

where $N_2$ equals a number of samples taken during a given measurement period, which can equal or be different from $N_1$ indicated above. After determining the intensity value, if so desired, the intensity value can be scaled, such as to within a range from 0 to 100.

In contrast to intensity activities, for each step activity, the activity detection application 30 can detect each step of the user in performing the respective activity, as shown in block 48. As the user performs the activity, then, the activity detection application can track the number of steps taken by the user, as well as the speed with which the user takes the steps. Although the activity detection application can detect each step in any of a number of different manners, in one embodiment, the activity detection application detects each step by first bandpass filtering the accelerometer measurements. For example, the activity detection application can finite impulse response (FIR) filter the measurements, normalizing the filtered measurements to avoid overflow, if so desired.

As will be appreciated by those skilled in the art, the activity detection application can detect steps of the user based upon the down-acceleration (x-axis) measurements without the back-acceleration (y-axis) measurements. In various embodiments, however, it may be desirable to detect steps of the user based upon the back-acceleration measurements, particularly in instances when the user moves at a very low walking speed. The following description, therefore, will focus on the down-acceleration measurements, although it should be understood that the activity detection application can equally process the back-acceleration measurements in the same manner as the down-acceleration measurements, if so desired.

In one more particular embodiment, the activity detection application 30 can pass the down-acceleration measurements through the following FIR filter:

$$\hat{x}_i = \frac{1}{C_1}\sum_{k=0}^{m-1} h_k x_{i-k},$$

where $h_k$ comprises each of m (e.g., m=16) filter taps, and $C_1$ comprises a constant (e.g., 2048). The FIR filter can include any of a number of different filter taps to realize the filter. For example, the FIR filter can include a set of filter taps for each step activity, such as one set of filter taps for walking activity and another set for running activity. In this regard, the filter taps for walking activity can realize a bandpass filter with cutoff frequencies at 0.1 and 4 Hz, while the filter taps for running activity can realize a bandpass filter with cutoff frequencies at 0.1 and 2 Hz.

After filtering the measurements, the activity detection application 30 can compute a threshold value from the filtered measurements. More particularly, for example, the activity detection application can determine a threshold, T, in accordance with the following:

$$T = \frac{C_2}{N_1}\sum_{k=i-N_1}^{i} |x_k|, \; C_2 = \begin{cases} 2/4 \text{ if walking} \\ 3/4 \text{ if running} \end{cases},$$

where $N_1$, as before, equals a number of samples in a sample window block (e.g., 128 samples), where the mean computation in determining the threshold, T, can be performed once per sample window block. As will be appreciated, if so desired, the threshold can be configured to have a minimum value (e.g., $T_{MIN}=25$) to eliminate step detection from very low measurements, such as when the terminal 10 is resting on a desk.

After filtering measurements and computing the threshold value, then, the activity detection application 30 can detect steps by comparing the filtered measurements and the threshold value. More particularly, for example, the activity detection application can operate a state machine whereby $S_0$ represents the state when a measurement is greater than a respective threshold value, and $S_1$ represents the state when the measurement is less than the negative threshold value. From the states, then, the activity detection application can detect a step each time the state transitions from $S_1$ to $S_0$, i.e., each time the measurements that are less than the negative threshold value increase to being greater than the threshold value. Because the activity detection application can receive one or more sporadic measurements that can indicate a step when the user has not actually taken a step, if so desired, state $S_1$ can include a timeout (e.g., one second) such that if the measurements are not greater than the threshold within the timeout, state $S_0$ is entered without a corresponding step detection.

In addition to detecting each step, the activity detection application 30, as indicated above, can determine a speed at which the user performs the step activity, as also shown in block 48. For example, the activity detection application can determine a speed by determining the rate at which the activity detection application detects each step. The step rate can then be multiplied by the step length for the user when performing the respective step activity (e.g., walking, run-ning, etc.), where the step length can be input by the user with other personal information (see block 36). Further, the activity detection application can determine the distance over which the user has performed the selected activity. For example, the activity detection application can determine distance by multiplying the number of detected steps by the step length for the respective activity.

As will be appreciated, the activity detection application 30 determines or computes a number of different values or pieces of physiological information for each type of selected activity, whether an intensity activity, duration activity or step activity. It should be understood, however, that irrespective of the type of selected activity, the activity detection application can determine or compute the pieces of physiological information for any one or more of the other activity types, without departing from the spirit and scope of the present invention. For example, irrespective of the activity type, the activity detection application can be capable of determining or computing any one or more of the heart rate of the user, the intensity value, the duration of the activity, the number of detected steps, the speed at which the user performs the activity and/or the distance over which the user performs the activity.

At one or more points in time, as or after the activity detection application 30 determines or computes one or more of the aforementioned pieces of physiological information, the activity detection application can compute the energy expended by the user in performing the selected activity, as shown in block 50. In this regard, as indicated above, the activity detection application can compute the energy expended based upon the activity, and further based upon the type of activity. In addition, the activity detection application can determine the energy expended by the user in performing a duration activity further based upon a basal metabolic rate (BMR) of the user, a metabolic equivalent (MET) and the duration over which the user performed the activity. More particularly, the activity detection application can determine the MET based upon the activity, and further based upon the intensity value when the selected activity has an intensity activity type, and further based upon the speed when the selected activity has a step activity type. Written notationally, then, the activity detection application can determine the number of calories expended by the user in accordance with one of the following:

Calories$_{duration}$=BMR×MET(activity)×time

Calories$_{intensity}$=BMR×MET(activity, intensity)×time

Calories$_{step}$=BMR×MET(activity, speed)×time

The BMR and MET can be determined in any of a number of different manners. For example, the BMR can be determined based upon the gender, age and weight of the user, each of which can be input with other personal information of the user (see block 36). More particularly, the BMR can be determined from World Health Organization equations predicting the BMR based upon the age and weight of the user. For example, for males ages 18-30, the BMR can be determined as follows:

$BMR_{18-30}$=15.3×weight+679 where weight can be expressed in kilograms.

Like the BMR, the MET can be determined in any of a number of different manners. As will be appreciated MET values are typically defined as the energy cost of an activity, and comprise multiples of the BMR for different activities. The MET values for duration activities, for example, can comprise constant multipliers based upon the respective activity, where the constant can be determined from empirical analysis, studies or the like. For intensity activities, the MET can be determined based upon a relationship between the energy cost and intensity value for the selected activity. Thus, from empirical analysis, studies or the like, a relationship can be determined between MET and intensity, I, for each selectable activity. Although any order relationship can be determined between MET and intensity, I, in one embodiment a linear relationship can be determined that has the following form:

$$MET(\text{activity, intensity}) = C_3 \times I + C_4$$

In the preceding equation, $C_3$ and $C_4$ represent constants for the selected activity that define the linear relationship, both of which, as indicated above, can be determined from empirical analysis, studies or the like. As will be appreciated, in various instances it may be desirable to bound the relationship between MET and I to within minimum and maximum values, i.e., $MET_{MAX}$, $MET_{MIN}$ and $I_{MAX}$, $I_{MIN}$. In such instances, $C_3$ and $C_4$ can be set equal to zero when the intensity, I, is below $I_{MIN}$. And when I exceeds $I_{MAX}$, $C_3$ can be set equal to zero, while $C_4$ is set equal to $MET_{MAX}$.

In contrast to the MET for intensity activities, the MET for step activities can be determined by weighting the speed of performing the selected activity based upon the selected activity. More particularly, for example, the MET for step activities can be determined as follows:

$$MET(\text{activity, speed})_{walking} = 0.4930 \times \text{speed}$$

$$MET(\text{activity, speed})_{running} = 1.0 \times \text{speed}$$

where speed can be expressed in kilometers per hour (km/h).

As the activity detection application 30 operates and determines or computes the various pieces of physiological information, the activity detection application can record one or more pieces of physiological information, such as in the database 32 of the terminal 10. For example, as shown in block 52, the activity detection application can record the heart rate, energy expended, duration, distance and/or detected steps for the user in performing the selected activity. As shown in block 54, during operation, the activity detection application can continuously receive measurements from the accelerometer, and determine or compute different pieces of physiological information for the user in performing the selected activity.

The pieces of physiological information recorded by the activity detection application 30 can thereafter be compared to goals of the user. For example, the recorded heart rate, energy expended, duration, distance and/or detected steps can be compared to goals for heart rate, energy expended, duration, distance and/or detected steps, respectively. In this regard, either as or after the user inputs, and the activity detection application receives, personal information of the user, the user can input, and the activity detection application can receive, goals of the user relating to one or more selected activities. For example, the activity detection application can receive goals such as a desired heart rate for performing an activity, amount of energy expended, duration of performing an activity, distance over which to perform the activity and/or number of steps in performing the activity. As will be appreciated, the goals can be received for any of a number of different time periods, such as for a single activity, or one or more activities performed over a day, week, month, year, etc.

In addition to the pieces of physiological information recorded over a given time period, and/or the goals for the respective pieces of physiological information of the given time period, the activity detection application 30 can be capable of presenting the comparison of the goals of the user and the user's progress toward those goals. For example, as shown in FIGS. 4A-4D, the activity detection application can drive the display 16 to present a graphical representation of a goal of the user, such as in the form of a closed loop 56. As shown, the closed loop includes, or is broken into, a plurality of sections 58, where each section represents a successive percentage of the goal. In this regard, starting from one of the sections, each successive adjacent block in a given direction from the starting section 58a can represent a successive percentage of the goal. For example, for a goal of 2,000 calories represented by a closed loop including 20 sections, each section can represent 5% of the goal, or 100 calories. In this regard, starting section can represent the first 5%, with the section 58b to the immediate right of the starting section representing the second 5% (i.e., 10%) of the goal, the section 58c to the immediate right of section 58b representing the third 5% (i.e., 15%), and so forth.

As the activity detection application 30 identifies when the user meets each successive percentage of a goal, such as by comparing the goal to the respective recorded pieces of physiological information, the activity detection application can drive the display 16 to alter the respective section of the closed loop representation of the goal in response to the user meeting the successive percentage. The activity detection application can alter the respective section in any of a number of different manners. In one embodiment shown in FIGS. 4B-4C, for example, the activity detection application drives the display to change the color of the respective section, such as by changing the color from white, open or otherwise colorless to black, in response to the user meeting the successive percentage of the goal.

In addition to presenting a graphical representation of the goal and the user's progression toward a goal for a given time period, the time period can be increased or decreased for different time periods and the user's progression presented relative to those time periods. For example, a user's daily goal to walk 10,000 steps can be converted to a weekly goal by multiplying the daily goal by seven days per week (i.e., 70,000 steps), a monthly goal by multiplying the daily goal by thirty days per month (i.e., 300,000 steps), and so forth. Alternatively, for example, a user's daily goal to walk 10,000 steps can be converted to an hourly goal by dividing the daily goal by twenty-four hours per day (i.e., 417 steps), a minute goal by dividing the daily goal by 1440 minutes per day (i.e., 7 steps), and so forth. The pieces of physiological information relating to the respective goal can then be recorded and collected over the respective time period(s) and presented in relation to the respective goal(s), such as in a manner shown in FIGS. 4A-4D. Additionally or alternatively, the pieces of physiological information relating to the respective goal can be presented in one or more other manners. For example, as shown in FIG. 5, the pieces of physiological information can be presented in a bar graph of pieces of physiological information over a number of successive time periods.

As indicated above, the activity detection application 30 can present, and receive an "automatic detection" selection that, upon being selected, causes the activity detection application to detect an activity as the user performs the activity. In one typical embodiment, for example, one or more activities can be defined by identifiers (e.g., RFIDs). In this regard, the respective activities can be "tagged" or otherwise received by the terminal 10, such as by an RFID tag or other short range communication means (e.g., access point) at or proximate a location (or device, machine or the like) where the terminal user may perform the respective activities. Thereafter, a respective activity can be recalled based upon the identifier provided to the terminal by the RFID tag or other short range communication means. For example, consider a wireless access point located proximate a tennis court of a tennis facility, where the access point is adapted to transmit an identifier defining the activity of tennis. In this instance, the activity detection application can receive the identifier to thereby detect the selected activity as tennis when the selected activity comprises "automatic detection" and the terminal user enters the tennis facility to thereby bring the terminal within range of the access point.

In another embodiment, for example, the activity detection application can detect an activity from the user being inactive, or performing a walking or running activity. In this regard, over a sample window block (e.g., N=50), the mean absolute values for the down-acceleration (x-axis) and back-acceleration (y-axis) measurements can be computed, such as in accordance with the following:

$$x_{mean}, y_{mean} = \frac{1}{N} \sum_{k=i-N}^{i} |x_k, y_k|$$

Then, for each pair $[X_{mean}, y_{mean}]$, the activity detection application can determine the squared Euclidian distance, d, to a predefined centroid associated with each of the detectable activities. In this regard, each activity can have an associated coordinate pair of centroid values. The walking activity, for example, can have the following centroid coordinate pair: $C_x$=120, $C_y$=70. Written notationally, then, for each detectable activity, the distance d can be determined as follows:

$$d=(x_{mean}-C_x)^2+(y_{mean}-C_y)^2$$

After determining the distance d to the centroid associated with each of the detectable activities, the activity detection application can select the activity having the shortest distance as the detected activity.

As will be appreciated, in various instances, the terminal 10 may be operating (having executed or otherwise initiated the activity detection application 30) at locations other than those proximate to a user performing a selected or detected activity, such as when the terminal is positioned at a storage location. The activity detection application can therefore be configured to determine, from measurements received from the accelerometer, the position of the terminal to thereby facilitate the activity detection application in identifying when the user is performing an activity, and when the terminal is operating during periods of inactivity of the user. From such a determination, then, the activity detection application can further compute the duration of time the user is actually inactive when the terminal is operating.

As indicated above, the terminal 10 can include one or more of the sensors 34 comprising a two or three-axis acceleration sensor (accelerometer). In instances in which the terminal includes a three-axis accelerometer, the activity detection application 30 can further receive measurements from all three axes to thereby determine a posture of the terminal when the terminal is operating. By determining the posture, the activity detection application can determine when the terminal is operating during periods of inactivity of the user independent of the orientation of the terminal. Further, the activity detection application can determine the posture of the user when an attachment position of the terminal to the user is known, such as to also permit the activity detection application to determine when the terminal is operating during periods of inactivity.

As indicated above, the activity detection application 30 can be capable of managing the user's personal fitness goals. In this regard, as also indicated above, the activity detection application can drive the display to present those goals, as well as the user's progression toward such goals. It should be understood, however, that the activity detection application can also dynamically adjust one or more goals of the user based upon the user's progression toward those goals. For example, presume that a user has a weekly goal of walking 70,000 steps that can be subdivided into a daily goal of 10,000 steps. Also, presume that over the first five days of the week the user has only walked a total of 10,000. In such instances, the activity detection application can adjust the daily goal of the user over the remaining two days of the week to 30,000 steps per day. By adjusting the daily goal to 30,000 steps per day, the user can meet the weekly goal of 70,000 steps by meeting the adjusted daily goal over the remaining two days of the week.

Figure 6A:
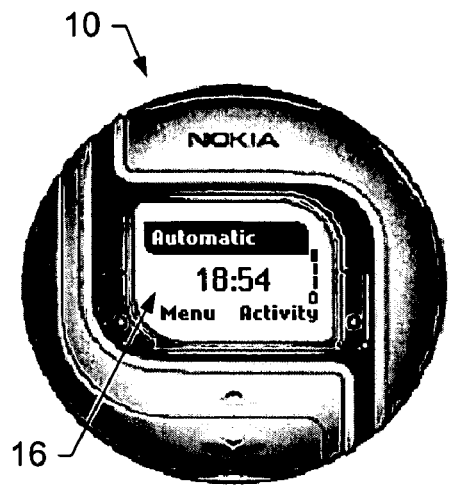
Figure 6B:
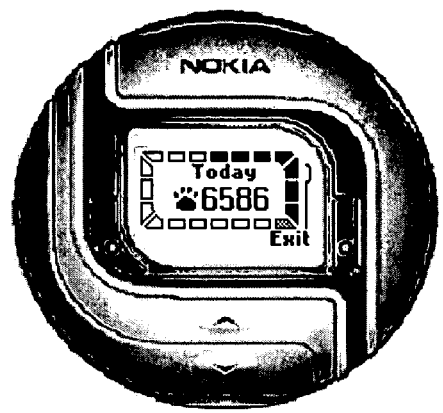
Figure 6C:
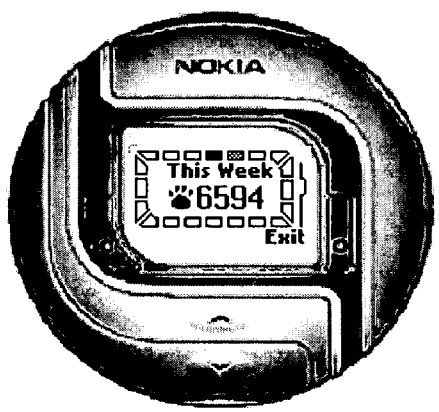

Reference is now made to FIGS. 6A-6C, 7, 8A-8D, 9A-9D, 10, 11, 12A-12D, 13 and 14, which illustrate the terminal 10 of embodiments of the present invention and various exemplar displays presented during operation of the terminal. As shown in FIG. 6A, upon activation of the activity detection application 30, the activity detection application can drive the display 16 to present a portal that indicates a current selected activity (e.g., "Automatic"), as well as the time (e.g., "18:54") and soft keys capable of being selected to activate menu and activity selection functions. From the portal, the user can scroll through a number of different displays, including a display presenting a graphical representation of the user's progression toward a daily goal (FIG. 6B) and/or a weekly goal (FIG. 6C), such as in the same manner as described above with respect to FIGS. 4A-4D. As shown in FIGS. 6B and 6C, in addition to presenting the user's progression, the display can present the current piece of physiological information for the respective computation over the given time frame, such as the current step count (indicated by a footprint) for the current day (e.g., 6586 as in FIG. 6B) and/or the current week (e.g., 6594 as in FIG. 6C).

Figure 7:

Also during operation, the user can be capable of selecting one of the soft keys presented by the display 16 (e.g., "Menu" and "Activity"), such as via the user input interface. As shown in FIG. 7, for example, upon selecting the "Activity" soft key, the user can be presented with a list of activities, such that the activity detection application 30 can thereafter receive a selection of one of the activities from the list (the currently selected activity being presented by the portal (see FIG. 6A). Upon selecting the "Menu" soft key, on the other hand, the user can be presented with a number of menu functions, including a "Results" function (FIGS. 8A-8D), a "Goals" function (FIGS. 9A-9D), a "Personal Information" function (FIG. 10), a "Step Information" function (FIG. 11), a "Settings" function (FIGS. 12A-12D), an "Extras" function (FIG. 13), and/or a "Data Transmission" function (FIG. 14).

Figure 8A:
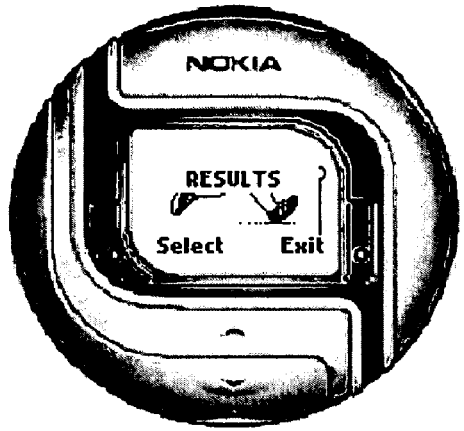
Figure 8B:
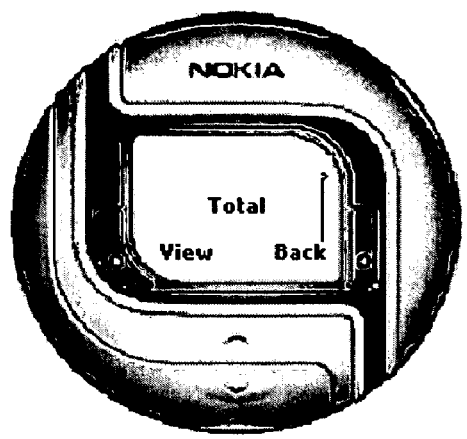
Figure 8C:
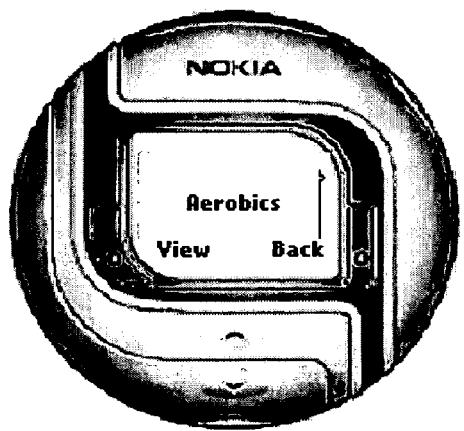
Figure 8D:
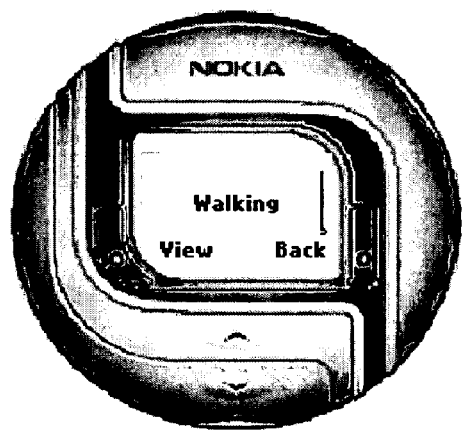

As shown more particularly in FIGS. 8A-8D, for example, upon selecting the "Results" function, the activity detection application 30 can drive the display 16 to present the total energy expended by the user in performing all selected activities over one or more time periods (FIG. 8B), and/or the energy expended by the user in performing individual selected activities over one or more time periods (aerobics shown in FIG. 8C and walking shown in FIG. 8D).

Figure 9A:
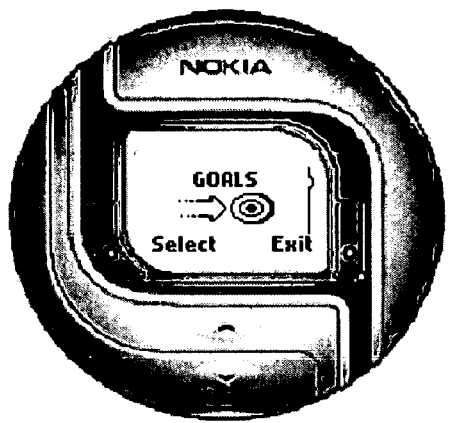
Figure 9B:
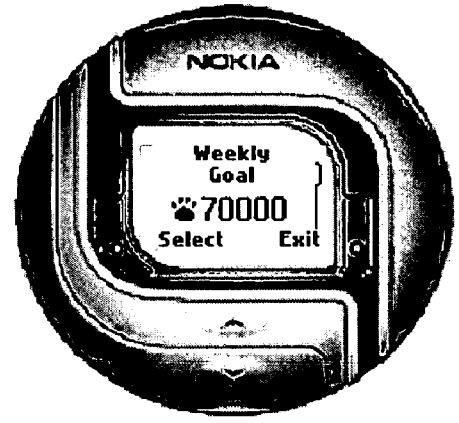
Figure 9C:
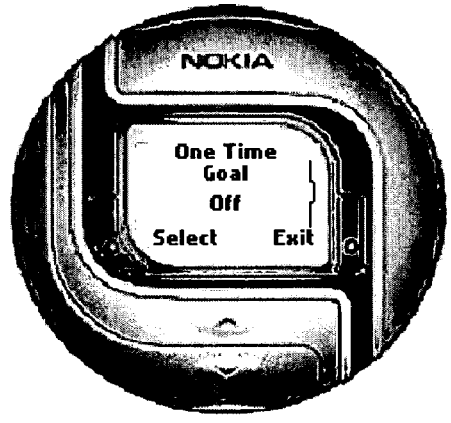
Figure 9D:
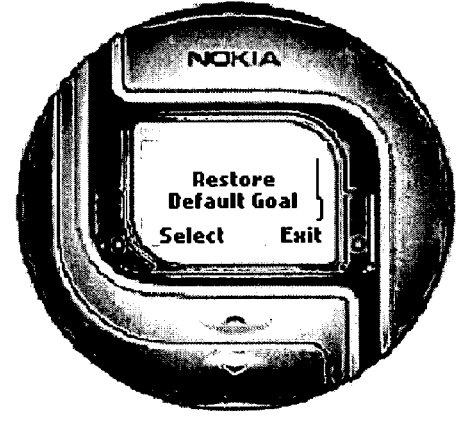

As shown in FIGS. 9A-9D, for example, upon selecting the "Goals" function, the activity detection application 30 can drive the display 16 to present the current weekly goal (e.g., 70000 steps, as shown in FIG. 9B). From the display of the current weekly goal, then, the user can be capable of selecting and modifying the goal, such as by modifying the value of the goal or the type of goal (e.g., energy expended, duration, steps, distance, etc.). In addition to presenting the weekly goal, the "Goals" function can also permit the user to set a one-time goal, such as for energy expended, duration, steps, distance, etc. And as will be appreciated, in lieu of setting a personal goal, the user can elect to set one or more goals based upon default settings that can be pre-stored within the terminal 10, as shown in FIG. 9D. For example, the terminal 10 can store, and the user can elect, one or more predefined goals, such as to maintain the user in good health.

Figure 10:
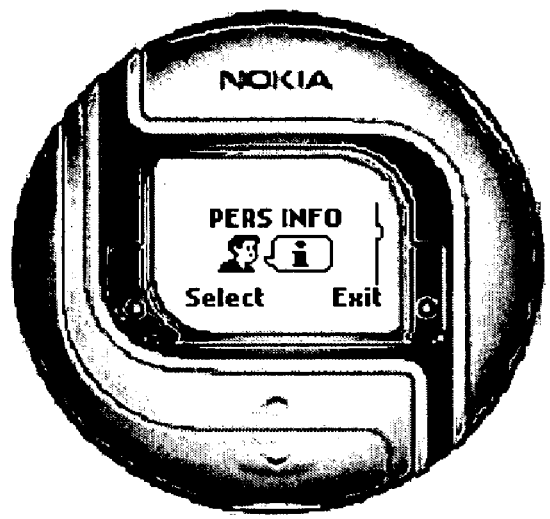
Figure 11:
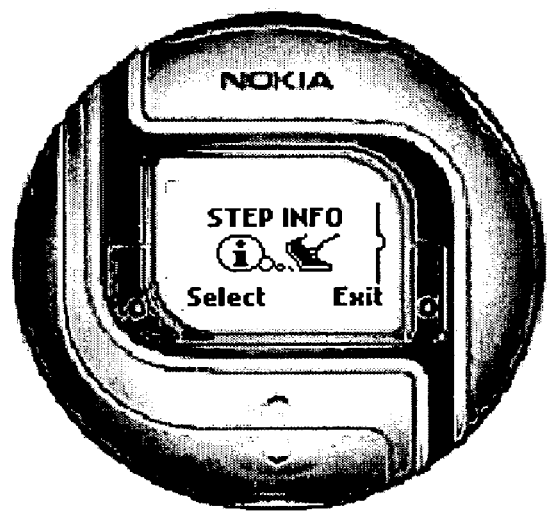

As shown briefly in FIG. 10, upon selecting the "Personal Information" function, the activity detection application 30 can drive the display 16 to request, and thereafter receive from the user, personal information such as date of birth, gender, height and/or weight. For additional personal information, the user can select the "Step Information" function, as shown briefly in FIG. 11. Upon selection of the "Step Information" function, the activity detection application can drive the display to request, and thereafter receive from the user, a step length for the user when walking and/or running.

Figure 12A:
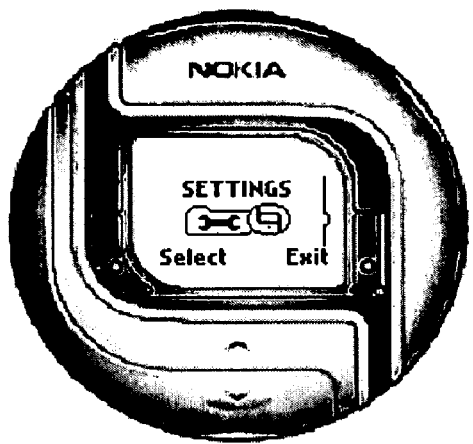
Figure 12B:
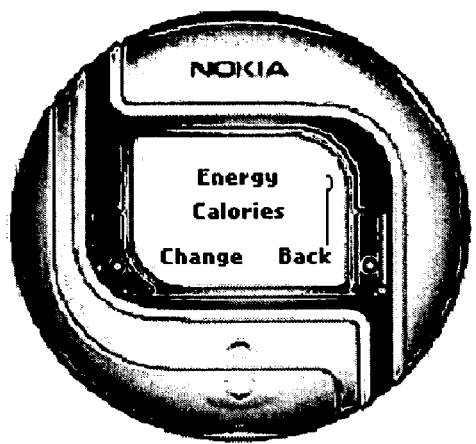
Figure 12C:
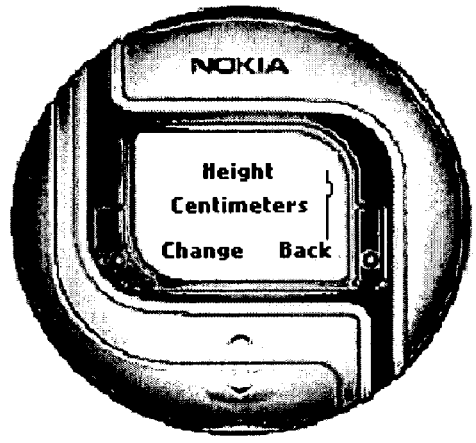
Figure 12D:
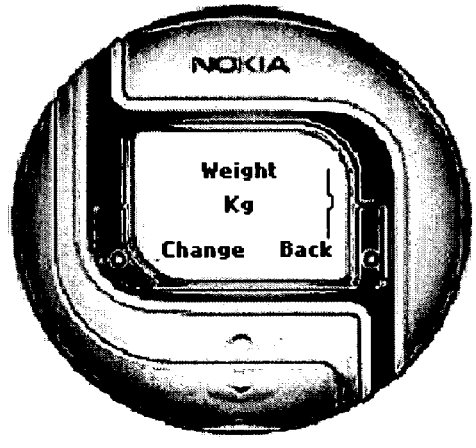

It should be noted that many of the pieces of physiological information measured, determined and/or computed in accordance with embodiments of the present invention have associated units. In this regard, upon selecting the "Settings" function, as shown in FIGS. 12A-12D, the user can be capable of choosing the units to associate with one or more pieces of physiological information. For example, as shown in FIG. 12B, the user can be capable of selecting the units to associate with energy expended by the user (e.g., "Calories"). As shown in FIG. 12C, the user can be capable of selecting the units to associate with the user's height (e.g., "Centimeters"); and as shown in FIG. 12D, the user can be capable of selecting the units to associate with the weight of the user (e.g., "kilograms").

Figure 13:
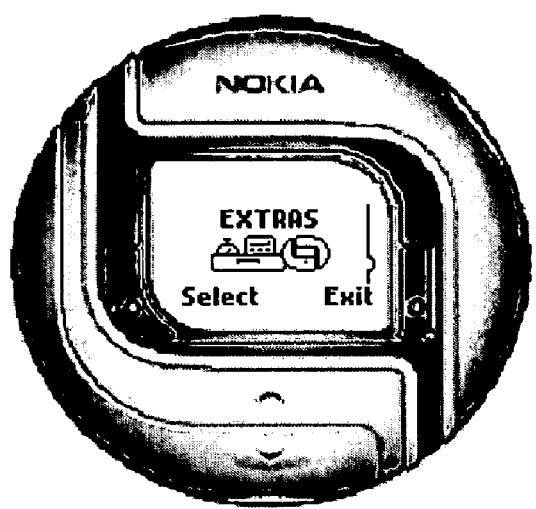
Figure 14:
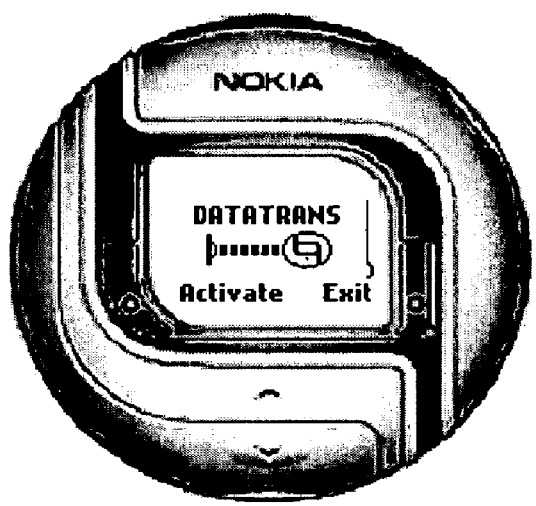

As shown briefly in FIG. 13, upon selecting the "Extras" function, the activity detection application 30 can drive the display 16 to request, and thereafter receive from the user, a selection of one or more extra functions of the terminal 10. In this regard, in addition to operating the activity detection application 30, the terminal can be capable of performing one or more additional, or extra, functions. For example, the terminal can include, and be capable of operating, a global positioning system (GPS), a radio, a clock, a digital music (e.g., MP3) player, PDA, organizer, mobile telephone or the like.

Further, as shown briefly in FIG. 14, upon selecting the "Data Transmission" function, the activity detection application 30 can communicate with one or more one or more means for sharing and/or obtaining data from electronic devices, such as a RF transceiver 20, IR transceiver 22, Bluetooth transceiver 24 or the like (see FIG. 1), to thereby transmit and/or receive data. In this regard, the terminal 10 can be capable of communicating with a mobile station, terminal or the like, such as that disclosed by Great Britain (GB) Patent Application No. 0326387.8, entitled: *Apparatus and Method for Providing a User with a Personal Exercise Program*, filed Nov. 12, 2003, the contents of which are hereby incorporated by reference in its entirety. In communicating with a mobile station, the terminal of embodiments of the present invention can be capable of sending data to the mobile station, such as pieces of physiological information computed during operation of the activity detection application 30 (e.g., energy expended, duration, steps, distance, etc.), for subsequent use by the mobile station. Additionally, or alternatively, the terminal of embodiments of the present invention can be capable of receiving data from the mobile station, such as goal settings, and/or BMR, MET, other activity-dependent values or the like.

Referring to FIG. 15, an illustration of one type of system that would benefit from the terminal 10 of embodiments of the present invention is provided. The system will be primarily described in conjunction with mobile communications applications. It should be understood, however, that the system can be utilized in conjunction with a variety of other applications, both in the mobile communications industries and outside of the mobile communications industries. For example, the system of embodiments of the present invention can be utilized in conjunction with wireline and/or wireless network (e.g., Internet) applications.

As shown, the terminal 10 is capable of interfacing with a mobile station 60, such as the mobile station disclosed by GB 0326387.8, in accordance with techniques such as, for example, radio frequency (RF), Bluetooth (BT), infrared (IrDA) or any of a number of different wireless networking techniques, including WLAN techniques. It should be understood, however, that although the terminal and mobile station are shown and described herein as comprising separate components of the system of FIG. 15, one or more entities may support both the terminal and the mobile station, logically separated but co-located within the entit(ies), without departing from the spirit and scope of the present invention. For example, a terminal may be capable of also functioning as a mobile station, or a mobile station may also be capable of functioning as a terminal.

The mobile station 10 may include an antenna 62 for transmitting signals to and for receiving signals from a base site or base station (BS) 64. Additionally or alternatively, the terminal may include an antenna for transmitting signals to and for receiving signals from a BS. In either event, the base station is a part of one or more cellular or mobile networks that each include elements required to operate the network, such as a mobile switching center (MSC) 66.

As well known to those skilled in the art, the mobile network may also be referred to as a Base Station/MSC/Interworking function (BMI). In operation, the MSC is capable of routing calls to and from the mobile station when the mobile station is making and receiving calls. The MSC can also provide a connection to landline trunks when the mobile station is involved in a call. In addition, the MSC can be capable of controlling the forwarding of messages to and from the mobile station, and can also control the forwarding of messages for the mobile station to and from a messaging center, such as short messaging service (SMS) messages to and from a SMS center (SMSC) 67.

The MSC 66 can be coupled to a data network, such as a local area network (LAN), a metropolitan area network (MAN), and/or a wide area network (WAN). The MSC can be directly coupled to the data network. In one typical embodiment, however, the MSC is coupled to a GTW 68, and the GTW is coupled to a WAN, such as the Internet 70. In turn, devices such as processing elements (e.g., personal computers, server computers or the like) can be coupled to the mobile station 60, and thus the terminal 10, via the Internet. For example, as explained below, the processing elements can include one or more processing elements associated with an origin server 72 or the like, one of which being illustrated in FIG. 15.

The BS 14 can also be coupled to a signaling GPRS (General Packet Radio Service) support node (SGSN) 74. As is well known, the SGSN is typically capable of performing functions similar to the MSC 66 for packet switched services. The SGSN, like the MSC, can be coupled to a data network, such as the Internet 70. The SGSN can be directly coupled to the data network. In a more typical embodiment, however, the SGSN is coupled to a packet-switched core network, such as a GPRS core network 76. The packet-switched core network is then coupled to another GTW, such as a GTW GPRS support node (GGSN) 78, and the GGSN is coupled to the Internet. In addition to the GGSN, the packet-switched core network can also be coupled to a GTW 68. Also, the GGSN can be coupled to a messaging center, such as a multimedia messaging service (MMS) center (MMSC) 79. In this regard, the GGSN and the SGSN, like the MSC, can be capable of controlling the forwarding of messages, such as MMS messages. The GGSN and SGSN can also be capable of controlling the forwarding of messages for the mobile station, and thus the terminal 10, to and from the messaging center.

In addition, by coupling the SGSN 74 to the GPRS core network 76 and the GGSN 78, devices such as origin servers 72 can be coupled to the mobile station 60, and thus the terminal 10, via the Internet 80, SGSN and GGSN. In this regard, devices such as origin servers can communicate with the mobile station across the SGSN, GPRS and GGSN. For example, origin servers can provide content to the mobile station, such as in accordance with the Multimedia Broadcast Multicast Service (MBMS). For more information on the MBMS, see Third Generation Partnership Project (3GPP) technical specification 3GPP TS 22.146, entitled: *Multimedia Broadcast Multicast Service (MBMS)*, the contents of which are hereby incorporated by reference in its entirety.

Although not every element of every possible mobile network is shown and described herein, it should be appreciated that the mobile station 60, and thus the terminal 10, can be coupled to one or more of any of a number of different networks through the BS 14. In this regard, the network(s) can be capable of supporting communication in accordance with any one or more of a number of first-generation (1G), second-generation (2G), 2.5G and/or third-generation (3G) mobile communication protocols or the like. For example, one or more of the network(s) can be capable of supporting communication in accordance with 2G wireless communication protocols IS-136 (TDMA), GSM, and IS-95 (CDMA). Also, for example, one or more of the network(s) can be capable of supporting communication in accordance with 2.5G wireless communication protocols GPRS, Enhanced Data GSM Environment (EDGE), or the like. Further, for example, one or more of the network(s) can be capable of supporting communication in accordance with 3G wireless communication protocols such as Universal Mobile Telephone System (UMTS) network employing Wideband Code Division Multiple Access (WCDMA) radio access technology. Some narrow-band AMPS (NAMPS), as well as TACS, network(s) may also benefit from embodiments of the present invention, as should dual or higher mode mobile stations (e.g., digital/analog or TDMA/CDMA/analog phones).

In addition to, or in lieu of, interfacing the terminal with a mobile station 60, the terminal 10 can be coupled to one or more wireless access points (APs) 80. The APs can comprise access points configured to communicate with the terminal in accordance with techniques such as, for example, radio frequency (RF), Bluetooth (BT), infrared (IrDA) or any of a number of different wireless networking techniques, including WLAN techniques. Additionally, or alternatively, the terminal can be directly or indirectly (e.g., via a mobile station) coupled to one or more user processors 82. Each user processor can comprise a computing system such as personal computers, laptop computers or the like. In this regard, the user processors can be configured to communicate with the mobile station in accordance with techniques such as, for example, RF, BT, IrDA or any of a number of different wireline or wireless communication techniques, including LAN and/or WLAN techniques. One or more of the user processors can additionally, or alternatively, include a removable memory capable of storing content, which can thereafter be transferred to the terminal.

The APs 80 and the user processors 82 may be coupled to the Internet 70. Like with the MSC 66, the APs and user processors can be directly coupled to the Internet. In one advantageous embodiment, however, the APs are indirectly coupled to the Internet via a GTW 68. As will be appreciated, by directly or indirectly connecting the terminals 10 and the origin server 72, as well as any of a number of other devices, to the Internet, the terminals can communicate with one another, the origin server, etc., to thereby carry out various functions of the terminal, such as to transmit data, content or the like to, and/or receive content, data or the like from, the origin server.

Reference is now made to FIG. 16, which illustrates one type of mobile station 60 that would benefit from embodiments of the present invention. It should be understood, however, that the mobile telephone illustrated and hereinafter described is merely illustrative of one type of mobile station that would benefit from the present invention and, therefore, should not be taken to limit the scope of the present invention. While several embodiments of the mobile station are illustrated and will be hereinafter described for purposes of example, other types of mobile stations, such as PDAs, pagers, laptop computers and other types of electronic systems, can readily employ the present invention.

As shown, in addition to an antenna 62, the mobile station 60 includes a transmitter 84, a receiver 86, and a controller 88 that provides signals to and receives signals from the transmitter and receiver, respectively. These signals include signaling information in accordance with the air interface standard of the applicable cellular system, and also user speech and/or user generated data. In this regard, the mobile station can be capable of operating with one or more air interface standards, communication protocols, modulation types, and access types. More particularly, the mobile station can be capable of operating in accordance with any of a number of first generation (1G), second generation (2G), 2.5G and/or third-generation (3G) communication protocols or the like. For example, the mobile station may be capable of operating in accordance with 2G wireless communication protocols IS-136 (TDMA), GSM, and IS-95 (CDMA). Also, for example, the mobile station may be capable of operating in accordance with 2.5G wireless communication protocols GPRS, Enhanced Data GSM Environment (EDGE), or the like. Further, for example, the mobile station may be capable of operating in accordance with 3G wireless communication protocols such as Universal Mobile Telephone System (UMTS) network employing Wideband Code Division Multiple Access (WCDMA) radio access technology. Some narrow-band AMPS (NAMPS), as well as TACS, mobile stations may also benefit from the teaching of this invention, as should dual or higher mode phones (e.g., digital/analog or TDMA/CDMA/analog phones).

It is understood that the controller 88 includes the circuitry required for implementing the audio and logic functions of the mobile station 60. For example, the controller may be comprised of a digital signal processor device, a microprocessor device, and various analog-to-digital converters, digital-to-analog converters, and other support circuits. The control and signal processing functions of the mobile station are allocated between these devices according to their respective capabilities. The controller can additionally include an internal voice coder (VC) 88A, and may include an internal data modem (DM) 88B. Further, the controller may include the functionally to operate one or more software programs, which may be stored in memory (described below). For example, the controller may be capable of operating a connectivity program, such as a conventional Web browser. The connectivity program may then allow the mobile station to transmit and receive Web content, such as according to the Hypertext Transfer Protocol (HTTP) and/or the Wireless Application Protocol (WAP), for example.

The mobile station 60 also comprises a user interface including a conventional earphone or speaker 90, a ringer 92, a microphone 94, a display 96, and a user input interface, all of which are coupled to the controller 88. The user input interface, which allows the mobile station to receive data, can comprise any of a number of devices allowing the mobile station to receive data, such as a keypad 98, a touch display (not shown) or other input device. In embodiments including a keypad, the keypad includes the conventional numeric (0-9) and related keys (#, *), and other keys used for operating the mobile station. Although not shown, the mobile station can include a battery, such as a vibrating battery pack, for powering the various circuits that are required to operate the mobile station, as well as optionally providing mechanical vibration as a detectable output.

Like the terminal 10, the mobile station 60 can also include one or more means for sharing and/or obtaining data. For example, the mobile station can include a short-range RF transceiver or interrogator 100 so that data can be shared with and/or obtained from electronic devices in accordance with RF techniques. The mobile station can additionally, or alternatively, include other short-range transceivers, such as, for example an IR transceiver 102, and/or a Bluetooth (BT) transceiver 104 operating using Bluetooth brand wireless technology developed by the Bluetooth Special Interest Group. The mobile station can therefore additionally or alternatively be capable of transmitting data to and/or receiving data from electronic devices in accordance with such techniques, and/or in accordance with a number of different wireless networking techniques, including WLAN techniques such as IEEE 802.11 techniques or the like. Further like the terminal, the mobile station 60 can also include one or more sensors 107 (e.g., heart rate sensor, positioning sensor, touch sensor, audio sensor, compass sensor, ambient light sensor, an ambient pressure senor, ambient temperature sensor, acceleration sensor, etc.).

The mobile station 60 can further include memory, such as a subscriber identity module (SIM) 106, a removable user identity module (R-UIM) or the like, which typically stores information elements related to a mobile subscriber. In addition to the SIM, the mobile station can include other removable and/or fixed memory. In this regard, the mobile station can include volatile memory 108, such as volatile Random Access Memory (RAM) including a cache area for the temporary storage of data. The mobile station can also include other non-volatile memory 110, which can be embedded and/or may be removable. The non-volatile memory can additionally or alternatively comprise an EEPROM, flash memory or the like. The memories can store any of a number of pieces of information, and data, used by the mobile station to implement the functions of the mobile station. For example, the memories can store data, such as one or more pieces of physiological information received from the terminal. The memories can also store one or more applications capable of operating on the mobile station. For example, the memories can store client applications such as a fitness trainer application, a conventional Web browser, one or more messaging (e-mail, SMS, MMS, etc.) applications and/or a time management or calendar application. Also, as explained below, the memories can store a data manager capable of managing data, such as one or more pieces of data capable of being transmitted to and/or received from, the terminal 10.

In accordance with another aspect of the present invention, a system and method are provided for managing physiological information computed or otherwise derived by the terminal 10. As explained below, the terminal is capable of communicating with one or more destinations via a mobile station 60 to thereby permit the destination to receive physiological information from the terminal. The destination can thereafter manage or otherwise utilize the physiological information in any of a number of different manners. For example, the destination(s) can be capable of viewing the physiological information, as well as creating, modifying or otherwise customizing workout programs or routines, including setting reminders, alarms or the like (collectively referred to as "alerts") based upon a schedule of performing the activities of a workout program. In this regard, the destination(s) can be further capable of communicating with the terminal to transfer content to the terminal, such as the created, modified or otherwise customized workout programs or routines, and/or the alert(s). As such, the system and method of managing physiological information facilitate use of the terminal, while providing a better experience for a user of the terminal.

Reference is now drawn to FIG. 17, which illustrates a functional block diagram of a terminal 10, or more particularly the activity detection application 30 of a terminal, providing or otherwise transferring one or more pieces of physiological information to one or more destinations via a mobile station 60. To permit the terminal to transfer physiological information to destination(s) via the mobile station in accordance with embodiments of the present invention, the mobile station is capable of operating a data manager 112. The data manager is capable of interfacing the activity detection application of the terminal with one or more destinations including, one or more destinations local to the mobile station and/or one or more destinations remote from the mobile station. For example, the data manager can interface the activity detection application with local destinations such as a database 114 and/or one or more applications such as a fitness trainer application 116 and/or a calendar application 118. Also, for example, the data manager can interface the activity detection application with one or more remote destinations 120, such as one or more other terminals 10 and/or mobile stations, and/or one or more origin servers 72, user processors 82, or the like.

As will be appreciated, the data manager 112 of the mobile station 60 can directly interface the activity detection application 30 of the terminal 10 to the remote destination(s) 120. In one embodiment, however, the data manager indirectly interfaces the activity detection application to one or more remote destinations via a conventional web browser application 122 and/or one or more messaging applications 124, any one or more of which can comprise a local destination. In this regard, any one or more of the remote destinations can be capable of storing a database, and/or operating an application such as a fitness trainer application, calendar application, Web browser, and/or one or more messaging applications in much the same manner as the mobile station.

As shown and described herein, the data manager 112, fitness trainer 116, calendar application 118, Web browser 122 and messaging application(s) 124 each comprise software operated by the mobile station 60 and/or remote destination(s) 120. It should be understood, however, that the data manager, fitness trainer, calendar application, Web browser and messaging application(s) can alternatively comprise firmware or hardware, without departing from the spirit and scope of the present invention. Also, although the applications are shown and described as being local to the mobile station and destination(s), any one or more of the applications can alternatively be distributed from, and in communication with, the mobile station and/or destination(s), respectively, such as across the Internet 70. Further, as shown and described herein, content is provided or otherwise transferred from a terminal to one or more destinations via the mobile station, or vice versa. It should be understood, however, that the terms "providing" and "transferring" can be used herein interchangeably, and that providing or transferring content can include, for example, moving or copying content from the terminal to the destination(s) via the mobile station, without departing from the spirit and scope of the present invention.

The system, method and computer program product of embodiments of the present invention will now be described in more detail with respect to transferring physiological information from a terminal 10 to one or more destinations via a mobile station 60, and/or one or more destinations transferring content to the terminal via the mobile station. As described herein, a destination can comprise any entity (e.g., database 114, fitness trainer 116, calendar application 118, terminal(s) 10, mobile station(s), origin server(s) 72, user processor(s) 82, etc.) including or otherwise associated with a communication device. In this regard, a destination can comprise any entity capable of functioning in accordance with embodiments of the present invention to communicate with the terminal to receive content from the terminal, such as one or more pieces of physiological information, and/or to transfer content to the terminal, such as modified and/or customized workout schedules, and/or alert(s). As will be further appreciated, although functionally operating in different manners, the terminal or mobile station can, at different times, function as a destination.

Reference is now drawn to FIG. 18, which illustrates a flowchart including various steps in a method of managing physiological information computed or otherwise derived by the terminal 10. As shown in block 128, the method includes initiating transfer of one or more pieces of physiological information to one or more destinations.

The transfer of physiological information can be initiated in any of a number of different manners. For example, a user of the terminal and/or mobile station 60 can initiate the transfer, such as via a respective user interface. Additionally or alternatively, the terminal and/or mobile station can initiate the transfer based upon presence information indicative of the terminal user using the terminal during performance of a selected activity. In such instances, for example, the data manager 112 of the mobile station (or activity detection application 30 of the terminal) can be capable of monitoring presence information related to the user. Then, when the presence information indicates that the user is using the terminal during performance of a selected activity, the data manager can initiate the transfer of physiological information.

Presence information indicative of the user using the terminal 10 during performance of a selected activity can be received, determined or otherwise identified by the data manager 112 (or activity detection application 30) in any of a number of different manners. For example, the data manager can determine presence information indicative of the user using the terminal during performance of a selected activity based upon receiving a notification or other communication that the activity detection application is being operated to monitor one or more activities of the user, and/or to derive physiological information relating to the user during performance of one or more activities. In this regard, the data manager can determine presence information based upon the activity detection application automatically detecting a selected activity, as such may be determined when the selected activity is "automatic detection," and the activity detection application detects an activity, as explained above.

Additionally or alternatively, for example, the data manager 112 (or activity detection application 30) can determine presence information based upon a predefined time set for the user to perform the selected activity, as such may be identified from a calendar stored by the terminal 10, mobile station 60 and/or a destination, the calendar reflecting one or more workout schedules or routines. In this regard, the data manager can determine presence information by matching the current time with the predefined time set for the user to perform the selected activity. In another example, the data manager can determine presence information based upon a location of the terminal 10 (and thus terminal user) indicative of the user using the terminal during performance of an activity. For example, the data manager can receive the location of the terminal (and thus the user), and matching the location with a location where the user is capable of performing an activity (e.g., a gym), determine presence information indicative of the user using the terminal during performance of the activity at the location of the terminal.

Irrespective of how the transfer of physiological information is initiated, the physiological information can thereafter be transferred from the terminal 10, or more particularly the activity detection application 30 of the terminal, to the data manager of the mobile station 60, as shown in block 130. The physiological information can comprise any of a number of different pieces of information stored, computed or otherwise derived by the terminal. Likewise, the piece(s) of physiological information can be selected in any of a number of different manners, such as by a terminal user, mobile station user, the activity detection application and/or a data manager (described below).

For example, the physiological information can comprise any one or more pieces of personal information of the user (e.g., date of birth, gender, height, weight, step length for the user when walking and/or running, etc.), and/or a selection of one or more activities performed by the user (e.g., automatic detection, walking, running, dancing, gardening (outdoor housework), performing housework (indoor housework), or participating in aerobics, badminton, basketball, football, soccer, golf, weight training, hiking, jumping rope, squash, table tennis, tennis, Nordic training, squash, racquet ball, etc.). Additionally, or alternatively, the physiological information can comprise, for each selected activity, a time stamp reflecting when the user started performing the activity, the heart rate of the user, the intensity value associated with the user, the duration of the activity, the number of detected steps, the speed at which the user performs the activity, the distance over which the user performs the activity, and/or the energy expended by the user in performing the activity. Further, for example, the physiological information can additionally or alternatively comprise one or more goals of the user relating to one or more selected activities (e.g., desired heart rate, amount of energy expended, duration of performing an activity, distance over which to perform the activity and/or number of steps in performing the activity, over a day, week, month, year, etc.).

Irrespective of the exact physiological information transferred from the activity detection application 30 of the terminal 10, the physiological information can be transferred to the mobile station in any of a number of different manners, and in accordance with any of a number of different communication or transfer techniques. In one embodiment, for example, the physiological information can be transferred to the mobile station in accordance with any of a number of different short range communication techniques such as RF, BT or IrDA, or any of a number of different wireline and/or wireless networking techniques such as LAN and/or WLAN techniques.

As shown in block 132, upon receipt of the physiological information from the activity detection application 30 of the terminal 10, the data manager 112 of the mobile station 60 can transfer one or more pieces of the physiological information to one or more destinations. For example, the data manager can transfer piece(s) of the physiological information to one or more of a database 114, fitness trainer 116 and/or calendar application 118 local to the mobile station, and/or to one or more remote destinations 120 (e.g., terminal(s) 10, mobile station(s), origin server(s) 72, user processor(s) 82, etc.). Like the piece(s) of physiological information, the destination(s) can be selected in any of a number of different manners. For example, the destination(s) can be selected by the terminal user, mobile station user, the activity detection application and/or the data manager. More particularly, for example, the destination(s) can be selected by the activity detection application and/or the data manager based upon the piece(s) of physiological information to transfer to the respective destination(s).

Like transferring the physiological information from the terminal 10 to the mobile station 60, the piece(s) of physiological information can be transferred to the destination(s) in any of a number of different manners, and in accordance with any of a number of different communication or transfer techniques. In this regard, when transferring physiological information to remote destination(s) 120, the data manager 112 can transfer piece(s) of physiological information in accordance with any of a number of different cellular (e.g., 1G, 2G, 2.5G, 3G, etc.) communication techniques such as GPRS, EDGE, MBMS or the like, any of a number of different short range communication techniques such as RF, BT, IrDA or the like, and/or any of a number of different wireline and/or wireless networking techniques such as LAN and/or WLAN techniques. More particularly, for example, the data manager can transfer one or more pieces of the physiological information to remote destination(s) by sending the respective piece(s) of physiological information in an e-mail, SMS or MMS message through a respective messaging application 124 to the remote destination(s) via a respective messaging center, such as a respective e-mail server (e.g., origin server 72), SMSC 67 or MMSC 79 (see FIG. 15).

Irrespective of how the data manager 112 transfers the piece(s) of physiological information to the destination(s), the destination(s) can thereafter operate based upon the respective piece(s) of physiological information, as shown in block 134 of FIG. 18. For example, the destination(s) can store the piece(s) of physiological information, such as in a database. Also, for example, the destination(s) can present or otherwise display the piece(s) of physiological information for a user of the respective destination(s). Additionally or alternatively, one or more destination(s) can transfer or otherwise share one or more piece(s) of the physiological information with one or more other destination(s).

Further, for example, one or more destination(s) can receive the piece(s) of physiological information into an application, such as a fitness trainer application 116 and/or calendar application 118, which can be capable of performing one or more operations based upon the physiological information. In this regard, a fitness trainer application such as that disclosed by GB 0326387.8 can be capable of or otherwise adapted to receive piece(s) of the physiological information and, based upon the piece(s) of physiological information, generate an exercise program (including one or more selected activities) for a terminal user, guide the user through the exercise program, and/or modify, customize or otherwise adjust the program and/or the user's goals (goals with respect to the selected activities) based upon the user's progress through the exercise program, including the user's progress through one or more activities of the exercise program. In yet another example, a calendar application can generate an exercise schedule by scheduling the terminal user to perform one or more selected activities, such as those activities of an exercise program generated by a fitness trainer application. The exercise schedule can then be incorporated into the exercise program, if so desired. The calendar application can also be capable of setting one or more alerts based upon the exercise schedule to thereby facilitate the terminal user performing the activit(ies) of an exercise program, or more particularly performing the scheduled activit(ies) of the exercise program.

As explained, the destination(s) can be capable of performing one or more operations based upon the piece(s) of physiological information. It should be understood that one or more destination(s) can be capable of communicating with one or more other destination(s) to collectively perform those operation(s) based upon the piece(s) of physiological information, without departing from the spirit and scope of the present invention. For example, a fitness trainer application, local to (e.g., fitness trainer 116) or remote from the mobile station 60, can be capable of generating an exercise program. The fitness trainer application can also be capable of communicating with a calendar application, local to (e.g., calendar application 118) or remote from the mobile station, such that the calendar application can schedule the user to perform one or more selected activities, and/or set one or more alerts. Further, it should be understood that although operations are capable of being performed by different destinations, including different applications, a single destination can be capable of performing the operations of a plurality of destinations. For example, a fitness trainer application, local to or remote from the mobile station, can be capable of performing the operations of the fitness trainer application, as well as one or more operations of the calendar application, such as scheduling the terminal user to perform one or more selected activities.

As will be appreciated, in one or more instances, after performing one or more operations based upon the piece(s) of physiological information, one or more destinations may select or otherwise determine content to return or otherwise transfer to the terminal 10 based upon the operation(s) performed by the destination(s), as shown in block 136. For example, a fitness trainer application may have a new exercise program, and/or modifications or adjustments to an existing exercise program (including one or more activities of an existing program), to transfer to the terminal. Also, for example, the fitness trainer application may have new or adjusted goals for the terminal user with respect to selected activities of an exercise program, and/or other content related to an exercise program or the user's progress through the exercise program, to transfer to the terminal. In another example, a calendar application may have one or more alerts (e.g., reminders, alarms, etc.) to transfer to the terminal.

Irrespective of the content the destination(s) have to transfer to the terminal 10, in such instances, the destination(s) can transfer such content to the data manager 112 of the mobile station 60, such as in the same manner the data manager sent the physiological information to the respective destination(s), as shown in block 138. For example, the destination(s) can transfer content to the data manager in accordance with any of a number of different cellular (e.g., 1G, 2G, 2.5G, 3G, etc.) communication techniques such as GPRS, EDGE, MBMS or the like, any of a number of different short range communication techniques such as RF, BT, IrDA or the like, and/or any of a number of different wireline and/or wireless networking techniques such as LAN and/or WLAN techniques. Upon receipt of the content at the data manager, the data manager can transfer the content to the terminal 10, or more particularly the activity detection application 30 of the terminal. For example, the data manager can transfer the content to the activity detection application in the same manner as the terminal transferred the physiological information to the mobile station, as shown in block 140. In this regard, the data manager can transfer the content to the terminal in accordance with any of a number of different short range communication techniques such as RF, BT or IrDA, or any of a number of different wireline and/or wireless networking techniques such as LAN and/or WLAN techniques.

As shown in block 142, upon receipt of the content, the activity detection application 30 of the terminal 10 can thereafter operate based upon the content. For example, the activity detection application can store the content in memory, such as in the database 32. Also, for example, the activity detection application can present or otherwise notify the terminal user of one or more piece(s) of the content, such as by notifying the terminal user of adjustment(s) to an existing exercise program to thereby facilitate the terminal user in performing activities in accordance with the adjusted exercise program. Additionally or alternatively, for example, the activity detection application can modify a calendar of the terminal user stored by the terminal, the calendar being capable of reflecting one or more workout schedules or routines of the terminal user, including the schedule(s) or routines of the adjusted exercise program. Further, for example, the activity detection application can execute one or more alerts to further facilitate the terminal user performing one or more selected activities, or more particularly performing the scheduled activit(ies) of the exercise program.

Irrespective of whether the destination(s) have content to transfer to the terminal 10, the terminal can, but need not, continue to transfer physiological information to the destination(s), such as in the same manner described above, as shown in block 144. In this regard, upon initiating the transfer of physiological information, the terminal, or more particularly the activity detection application 30, can be adapted to transfer physiological information at a plurality of instances during performance of an activity by the terminal user. For example, the activity detection application can be adapted to transfer physiological information at the start and end of an activity, or at predefined intervals during performance of the activity. Likewise, then, the destination(s) can, but need not, continue to transfer content back to the terminal, such as during performance of an activity by the terminal user. For example, the destination(s) can be adapted to continuously modify or adjust an existing exercise program during the terminal user's performance of an activity of the exercise program, such as by adjusting the goals for the terminal user with respect to the activity based upon the user's progress through the activity, or more generally, the exercise program.

To further illustrate this aspect of the present invention, consider a user of both a terminal 10 and a mobile station 60 who has engaged a personal trainer possessing a communication device (i.e., destination) such as a personal computer, laptop computer, mobile telephone or PDA. The personal trainer has designed an exercise program (including at least one scheduled activity) for the terminal user, which the terminal user has stored on the terminal. For example, the exercise program can include the terminal user running for thirty minutes at a scheduled time. Before the terminal user begins performing the scheduled activity, the terminal user configures the activity detection application to begin transmitting physiological information to the personal trainer (or more precisely the communication device of the personal trainer) once the user begins performing the scheduled activity, and to continuously transmit the physiological information at five minute intervals during performance of the activity. In this instance, the physiological information can include, for example, the user's heart rate, intensity level and/or duration of performing the scheduled activity.

When the user begins performing the scheduled running activity, the activity detection application 30 of the user's terminal 10 transmits the user's heart rate, intensity level and/or activity duration to the user's mobile station 60 which, in turn, transmits the heart rate, intensity level and/or duration information to the communication device of the personal trainer. Then, at five minute intervals during the thirty minute run, the activity detection application continues to transmit physiological information to the personal trainer. The communication device can receive the physiological information and present the physiological information to the personal trainer such that the personal trainer is capable of monitoring the user's progress during the run. During the run, then, the personal trainer can be capable of adjusting or otherwise modifying the scheduled activity based upon the physiological information. For example, the personal trainer can modify the duration (e.g., increasing/decreasing the time from thirty minutes) of the selected activity, modify the selected activity (e.g., changing the activity from running to walking), and/or modify one or more other schedules activities of the exercise program (e.g., increasing/decreasing the duration of other scheduled activities, and/or modifying one or more other activities). After modifying the scheduled activity, the personal trainer, via the communications device and the user's mobile station, can transmit the modified schedule to the user, or more particularly the user's terminal. Upon receipt of the modified schedule, the activity detection application can notify the user of the modification (e.g., via an alert) such that the user can modify performance of the scheduled activity accordingly. Additionally or alternatively, the activity detection application can modify a calendar of the terminal user to reflect the modified schedule.

In another context, consider that, instead of engaging a personal trainer, the user of both a terminal 10 and a mobile station 60 desires to locate one or more partners of comparable physical condition for a one-time or routine tennis match. In such an instance, also consider that the intensity level of the respective participants in playing tennis can be representative of the physical condition of the respective participants. Also consider a Web-based service provider (i.e., destination) that provides a repository of physiological information of subscribers including the terminal user, and permits the terminal user to search for other subscribers also desiring a partner for a tennis match based upon physiological information of the subscribers, such as the intensity levels, maintained by the service provider.

In this context, the terminal user can initiate the transmission of the intensity level of the user playing tennis, to the service provider, where the intensity level can be transmitted as the terminal user plays tennis or at any point thereafter. Upon receipt of the intensity level, the service provider can store the intensity level in the repository maintained by the service provider. Additionally, in response to receipt of the intensity level of the user, the service provider can transmit a list of one or more other subscribers with comparable intensity levels back to the terminal and, if so desired, can include the mobile telephone numbers of the respective subscribers. The user can then contact one or more of the subscribers from the list to schedule the desired tennis match.

Further, consider that the user has played tennis with a partner, each using a respective terminal 10 during the match to compute or otherwise derive physiological information related to the respective participant, including the intensity level of the respective participant during the tennis match. After the tennis match, then, the participants can share physiological information, including the intensity levels, with one another. In this instance, the terminal of each participant is considered the destination of physiological information with respect to the terminal of the other participant. Thus, by exchanging physiological information after the tennis match, the participants can compare the physiological information of each other computed or otherwise derived during the tennis match.

According to one aspect of the present invention, all or a portion of the system of the present invention, such as all or portions of the terminal 10 mobile station 60 and/or destination(s) generally operates under control of a computer program product (e.g., activity detection application 30, data manager 112, etc.). The computer program product for performing the methods of embodiments of the present invention includes a computer-readable storage medium, such as the non-volatile storage medium, and computer-readable program code portions, such as a series of computer instructions, embodied in the computer-readable storage medium.

In this regard, FIGS. 3 and 18 are flowcharts of methods, systems and program products according to the invention. It will be understood that each block or step of the flowcharts, and combinations of blocks in the flowcharts, can be implemented by computer program instructions. These computer program instructions may be loaded onto a computer or other programmable apparatus to produce a machine, such that the instructions which execute on the computer or other programmable apparatus create means for implementing the functions specified in the flowcharts block(s) or step(s). These computer program instructions may also be stored in a computer-readable memory that can direct a computer or other programmable apparatus to function in a particular manner, such that the instructions stored in the computer-readable memory produce an article of manufacture including instruction means which implement the function specified in the flowcharts block(s) or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the flowcharts block(s) or step(s).

Accordingly, blocks or steps of the flowcharts support combinations of means for performing the specified functions, combinations of steps for performing the specified functions and program instruction means for performing the specified functions. It will also be understood that each block or step of the flowcharts, and combinations of block(s) or step(s) in the flowcharts, can be implemented by special purpose hardware-based computer systems which perform the specified functions or steps, or combinations of special purpose hardware and computer instructions.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system for managing physiological information, the system comprising:
   a mobile terminal comprising a processor configured to transfer physiological information relating to a user; and
   at least one apparatus receiving the physiological information and performing at least one operation based upon the physiological information, the at least one operation including adjusting an exercise program that includes a plurality of selected activities at least one of performed or to be performed by the user, wherein adjusting the exercise program includes adjusting at least one of a selected activity, or a parameter or a goal associated with a selected activity, wherein the at least one apparatus also returns content to the terminal, and wherein the content includes the adjusted exercise program, the content being selected based upon the at least one operation performed by the at least one apparatus,
   wherein the terminal processor is also configured to perform at least one operation based upon the content returned to the terminal, and
   wherein the terminal processor is configured to initiate the transfer of physiological information based upon presence information related to the user and at least one of the selected activities of the exercise program.

2. A system according to claim 1 further comprising:
   a mobile station comprising a processor configured to receive the physiological information from the terminal, and thereafter transmit the physiological information to the at least one apparatus, and wherein the mobile station processor is configured to receive the content from the at least one apparatus, and thereafter return the content to the terminal.

3. A system according to claim 1, wherein one of the terminal processor or the mobile station processor is configured to monitor presence information related to the user, and initiate the transfer when the presence information is indicative of the user performing at least one of the selected activities of the exercise program.

4. A system according to claim 3, wherein one of the terminal processor or the mobile station processor is configured to initiate the transfer when performance of at least one of the selected activities of the exercise program is detected.

5. A system according to claim 3, wherein one of the terminal processor or the mobile station processor is configured to initiate the transfer when a current time matches a predefined time set for the user to perform at least one of the selected activities of the exercise program.

6. A system according to claim 3, wherein one of the terminal processor or the mobile station processor is configured to initiate the transfer when a location of the terminal matches a location adapted for performing at least one of the selected activities of the exercise program.

7. A system according to claim 1, wherein the terminal processor is configured to perform at least one operation comprising notifying the user of the adjusted exercise program.

8. A system according to claim 7, wherein the terminal processor is configured to transfer physiological information, the at least one apparatus adjusting the exercise program and returning the adjusted exercise program to the terminal, and the terminal processor is configured to notify the user of the adjusted exercise program during performance, by the user, of at least one of the selected activities of the exercise program.

9. A system according to claim 1, wherein the terminal processor is configured to perform at least one operation comprising modifying a calendar of the user, the calendar reflecting at least one workout schedule of the adjusted exercise program.

10. A system according to claim 1, wherein the at least one apparatus performs at least one operation comprising setting at least one alert based upon an exercise schedule, and wherein the at least one apparatus returns the at least one alert to the terminal.

11. A system according to claim 10, wherein the terminal processor is configured to perform at least one operation comprising executing the at least one alert.

12. A system according to claim 10, wherein the at least one apparatus comprises at least one other mobile terminal including a processor, and wherein the at least one other mobile terminal processor is configured to return physiological information relating to at least one other user of the at least one other terminal.

13. A system according to claim 1, wherein the mobile terminal processor is further configured to derive the physiological information relating to the user.

14. A system according to claim 13, wherein the terminal processor is configured to initiate the transfer of physiological information based upon presence information related to the user, the presence information indicating that the mobile terminal processor is deriving physiological information relating to the user.

15. An apparatus comprising:
a processor configured to transfer physiological information and thereafter receiving, in response thereto, content following performance of at least one operation based upon the physiological information, wherein the at least one operation includes adjusting an exercise program and the received content includes the adjusted exercise program, wherein the exercise program includes a plurality of selected activities at least one of performed or to be performed by the user, and adjusting the exercise program includes adjusting at least one of a selected activity, or a parameter or a goal associated with a selected activity, wherein the content is selected based upon the at least one operation performed based upon the physiological information, wherein the processor is also configured to perform at least one operation based upon the received content, and wherein the processor is configured to initiate the transfer of physiological information based upon presence information related to the user and at least one of the selected activities of the exercise program.

16. An apparatus according to claim 15, wherein the processor is configured to monitor presence information related to the user, and initiate the transfer when the presence information is indicative of the user performing at least one of the selected activities of the exercise program.

17. An apparatus according to claim 16, wherein the processor is configured to initiate the transfer when performance of at least one of the selected activities of the exercise program is detected.

18. An apparatus according to claim 16, wherein the processor is configured to initiate the transfer when a current time matches a predefined time set for the user to perform at least one of the selected activities of the exercise program.

19. An apparatus according to claim 16, wherein the processor is configured to initiate the transfer when a location of the apparatus matches a location adapted for performing at least one of the selected activities of the exercise program.

20. An apparatus according to claim 15, wherein the processor is configured to transfer the physiological information to a mobile station such that the mobile station transfers the physiological information to at least one apparatus, and such that the at least one apparatus returns content to the mobile station, with the mobile station returning the content to the apparatus.

21. An apparatus according to claim 15, wherein the processor is configured to perform at least one operation comprising notifying the user of the adjusted exercise program.

22. An apparatus according to claim 21, wherein the processor is configured to transfer the physiological information, receive the adjusted exercise program, and notify the user of the adjusted exercise program during performance, by the user, of at least one of the selected activities of the exercise program.

23. An apparatus according to claim 15, wherein the processor is configured to perform at least one operation comprising modifying a calendar of the user, the calendar reflecting at least one workout schedule of the adjusted exercise program.

24. An apparatus according to claim 15, wherein the processor is configured to transfer physiological information to at least one apparatus such that the at least one apparatus sets at least one alert based upon an exercise schedule and returns the at least one alert to the apparatus.

25. An apparatus according to claim 24, wherein the processor is configured to perform at least one operation comprising executing the at least one alert.

26. An apparatus according to claim 24, wherein the processor is configured to transfer physiological information to at least one apparatus comprising at least one other apparatus such that the at least one other apparatus returns physiological information relating to at least one other user of the at least one other apparatus.

27. An apparatus according to claim 15, wherein the processor is further configured to derive the physiological information relating to the user.

28. An apparatus according to claim 27, wherein the processor is configured to initiate the transfer of physiological information based upon presence information related to the user, the presence information indicating that the processor is deriving physiological information relating to the user.

29. An apparatus comprising:
a processor configured to receive, from a mobile terminal, physiological information relating to a user, wherein the processor is also configured to transfer the physiological information and thereafter receive, in response thereto, content following performance of at least one operation based upon the physiological information, wherein the at least one operation includes adjusting an exercise program and the received content includes the adjusted exercise program, wherein the exercise program includes a plurality of selected activities at least one of performed or to be performed by the user, and adjusting the exercise program includes adjusting at least one of a selected activity, or a parameter or a goal associated with a selected activity, wherein the processor is configured to return the content to the terminal such that the terminal performs at least one operation based upon the content, the content being selected based upon the at least one operation performed based upon the physiological information, and wherein the processor is configured to initiate the transfer of physiological information based upon presence information related to the user and at least one of the selected activities of the exercise program.

30. An apparatus according to claim 29, wherein the processor is configured to monitor presence information related to the user, and initiate the transfer when the presence information is indicative of the user performing at least one of the selected activities of the exercise program.

31. An apparatus according to claim 30, wherein the processor is configured to initiate the transfer when performance of at least one of the selected activities of the exercise program is detected.

32. An apparatus according to claim 30, wherein the processor is configured to initiate the transfer when a current time matches a predefined time set for the user to perform at least one of the selected activities of the exercise program.

33. An apparatus according to claim 30, wherein the processor is configured to initiate the transfer when a location of the terminal matches a location adapted for performing at least one of the selected activities of the exercise program.

34. An apparatus according to claim 29, wherein the processor is configured for returning the adjusted exercise program to the terminal such that the terminal performs at least one operation comprising notifying the user of the adjusted exercise program.

35. An apparatus according to claim 34, wherein the processor is configured to receive physiological information, transfer the physiological information, receive the adjusted exercise program and thereafter return the adjusted exercise program to the terminal such that the terminal notifies the user of the adjusted exercise program, during performance of the at least one activity by the user.

36. An apparatus according to claim 29, wherein the processor is configured to return the adjusted exercise program to the terminal such that the terminal performs at least one operation comprising modifying a calendar of the user, the calendar reflecting at least one workout schedule of the adjusted exercise program.

37. An apparatus according to claim 29, wherein the processor is also configured to transfer the physiological information to at least one apparatus such that the at least one apparatus sets at least one alert based upon an exercise schedule, and wherein the processor is configured to receive the at least one alert from the at least one apparatus and thereafter return the at least one alert to the terminal.

38. An apparatus according to claim 37, wherein the processor is configured to return the at least one alert to the terminal such that the terminal performs at least one operation comprising executing the at least one alert.

39. An apparatus according to claim 37, wherein the at least one apparatus comprises at least one other mobile terminal, and wherein the processor is configured to receive, and return to the terminal, content comprising physiological information relating to at least one other user of the at least one other terminal.

40. An apparatus according to claim 29, wherein the processor is configured to receive physiological information derived by the mobile terminal.

41. An apparatus according to claim 40, wherein the processor is configured to initiate the transfer of physiological information based upon presence information related to the user, the presence information indicating that the mobile terminal is deriving physiological information relating to the user.

42. A method of managing physiological information relating to a user, the method comprising:
receiving physiological information from a mobile terminal, the physiological information being received in response to initiation of a transfer of the physiological information based upon presence information related to the user and at least one of the selected activities of the exercise program;
performing at least one operation based upon the received physiological information, the at least one operation including adjusting an exercise program, wherein the exercise program includes a plurality of selected activities at least one of performed or to be performed by the user, and adjusting the exercise program includes adjusting at least one of a selected activity, or a parameter or a goal associated with a selected activity; and
returning content to the terminal, wherein the returned content includes the adjusted exercise program, the content being selected based upon the at least one operation performed based upon the received physiological information, and wherein returning content comprises returning content such that the terminal performs at least one operation based upon the content returned to the terminal.

43. A method according to claim 42, wherein receiving physiological information comprises receiving physiological information in response to a monitoring of presence information related to the user,
and initiation of the transfer when the presence information is indicative of the user performing at least one of the selected activities of the exercise program.

44. A method according to claim 43, wherein receiving physiological information comprises receiving physiological information in response to initiation of the transfer when performance of at least one of the selected activities of the exercise program is detected.

45. A method according to claim 43, wherein receiving physiological information comprises receiving physiological information in response to initiation of the transfer when a current time matches a predefined time set for the user to perform at least one of the selected activities of the exercise program.

46. A method according to claim 43, wherein receiving physiological information comprises receiving physiological information in response to initiation of the transfer when a location of the terminal matches a location adapted for performing at least one of the selected activities of the exercise program.

47. A method according to claim 42, wherein receiving physiological information comprises receiving physiological information from a mobile terminal to a mobile station, and from the mobile station to at least one apparatus, and
wherein returning content to the terminal comprises returning content to the mobile station from the at least one apparatus, and from the mobile station to the terminal.

48. A method according to claim 42, wherein returning content comprises returning content such that the terminal notifies the user of the adjusted exercise program.

49. A method according to claim 48, wherein receiving physiological information, adjusting the exercise program, returning the adjusted exercise program to the terminal and notifying the user of the adjusted exercise program occur during performance, by the user, of at least one of the selected activities of the exercise program.

50. A method according to claim 42, wherein returning content comprises returning content such that the terminal modifies a calendar of the user, the calendar reflecting at least one workout schedule of the adjusted exercise program.

51. A method according to claim 42, wherein performing at least one operation comprises setting at least one alert based upon an exercise schedule, and
wherein returning content to the terminal comprises returning the at least one alert to the terminal.

52. A method according to claim 51, wherein returning content comprises returning content such that the terminal executes the at least one alert at the terminal.

53. A method according to claim 42, wherein receiving physiological information comprises receiving physiological information from a mobile terminal at at least one other mobile terminal, and
wherein returning content to the terminal comprises returning physiological information relating to at least one other user of the at least one other terminal.

54. A method according to claim 42, wherein receiving physiological information comprises receiving physiological information derived by the mobile terminal.

55. A method according to claim 54,
wherein receiving physiological information comprises receiving physiological information in response to initiation of the transfer of physiological information based upon presence information related to the user, the presence information indicating that the mobile terminal is deriving physiological information relating to the user.

56. A computer program product for managing physiological information, wherein the computer program product comprises at least one computer-readable storage medium having computer-readable program code portions stored therein, the computer-readable program code portions comprising:
a first executable portion for receiving physiological information from a mobile terminals, the physiological information being received in response to initiation of a transfer of the physiological information based upon presence information related to the user and at least one of the selected activities of the exercise program;
a second executable portion for performing at least one operation based upon the received physiological information, the at least one operation including adjusting an exercise program, wherein the exercise program includes a plurality of selected activities at least one of performed or to be performed by the user, and adjusting the exercise program includes adjusting at least one of a selected activity, or a parameter or a goal associated with a selected activity; and
a third executable portion for returning content to the terminal, wherein the returned content includes the adjusted exercise program, the content being selected based upon the at least one operation performed based upon the received physiological information, wherein the third executable portion is adapted to return content such that the terminal performs at least one operation based upon the content returned to the terminal.

57. A computer program product according to claim 56, wherein the first executable portion is adapted to receive physiological information in response to a monitoring of presence information related to the user,
and initiation of the transfer when the presence information is indicative of the user performing at least one of the selected activities of the exercise program.

58. A computer program product according to claim 57, wherein the first executable portion is adapted to receive physiological information in response to initiation of the transfer when performance of at least one of the selected activities of the exercise program is detected.

59. A computer program product according to claim 57, wherein the first executable portion is adapted to receive physiological information in response to initiation of the transfer when a current time matches a predefined time set for the user to perform at least one of the selected activities of the exercise program.

60. A computer program product according to claim 57, wherein the first executable portion is adapted to receive physiological information in response to initiation of the transfer when a location of the terminal matches a location adapted for performing at least one of the selected activities of the exercise program.

61. A computer program product according to claim 56, wherein the first executable portion is adapted to receive physiological information from the mobile terminal at a mobile station, wherein the computer program product further comprises:
a fourth executable portion for receiving the physiological information from the mobile station at at least one apparatus, wherein the third executable portion is adapted to transfer content to the mobile station from the at least one apparatus; and
a fifth executable portion for returning the content received by the mobile station to the terminal.

62. A computer program product according to claim 56, wherein the third executable portion is adapted to the third executable portion is adapted to return content such that the terminal notifies the user of the adjusted exercise program.

63. A computer program product according to claim 62, wherein the first executable portion is adapted to receive physiological information, the second executable portion is adapted to adjust the exercise program, and the third executable portion is adapted to return the adjusted exercise program to the terminal such that the terminal notifies the user of the adjusted exercise program during performance, by the user, of the at least one of the selected activities of the exercise program.

64. A computer program product according to claim 56, wherein the third executable portion is adapted to the third executable portion is adapted to return content such that the terminal modifies a calendar of the user, the calendar reflecting at least one workout schedule of the adjusted exercise program.

65. A computer program product according to claim 56, wherein the second executable portion is adapted to set at least one alert based upon an exercise schedule, and
wherein the third executable portion is adapted to return the at least one alert to the terminal.

66. A computer program product according to claim 65, wherein the third executable portion is adapted to return content such that the terminal executes the at least one alert at the terminal.

67. A computer program product according to claim 56, wherein the first executable portion is adapted to receive physiological information from a mobile terminal at at least one other mobile terminal, and
wherein the third executable portion is adapted to return physiological information relating to at least one other user of the at least one other terminal.

68. A computer program product according to claim 56, wherein the first executable portion is adapted to receive physiological information derived by the mobile terminal.

69. A computer program product according to claim 68, wherein the first executable portion is adapted to receive physiological information in response to initiation of the transfer of physiological information based upon presence information related to the user, the presence information indicating that the mobile terminal is deriving physiological information relating to the user.

70. A system for managing physiological information, the system comprising:
a mobile terminal comprising a processor configured to transfer physiological information relating to a user;
at least one apparatus receiving the physiological information and performing at least one operation based upon the physiological information, the at least one operation including adjusting an exercise program that includes a plurality of selected activities at least one of performed or to be performed by the user, wherein adjusting the exercise program includes adjusting at least one of a selected activity, or a parameter or a goal associated with a selected activity, wherein the at least one apparatus also returns content to the terminal, and wherein the content includes the adjusted exercise program, the content being selected based upon the at least one operation performed by the at least one apparatus; and
a mobile station comprising a processor configured to receive the physiological information from the terminal, and thereafter transmit the physiological information to the at least one apparatus, and wherein the mobile station processor is configured to receive the content from the at least one apparatus, and thereafter return the content to the terminal,
wherein one of the terminal processor or the mobile station processor is configured to initiate the transfer of physiological information based upon presence information related to the user and at least one of the selected activities of the exercise program, and
wherein the terminal processor is also configured to perform at least one operation based upon the content returned to the terminal.

* * * * *